(12) United States Patent  (10) Patent No.: US 8,377,020 B1
Berven  (45) Date of Patent: Feb. 19, 2013

(54) OSTOMY BAG WATERPROOF COVER AND METHOD

(76) Inventor: Marilyn Berven, Rochester, MN (US)

( * ) Notice: Subject to any disclaimer, the term of this patent is extended or adjusted under 35 U.S.C. 154(b) by 138 days.

(21) Appl. No.: 13/018,210

(22) Filed: Jan. 31, 2011

Related U.S. Application Data

(60) Provisional application No. 61/434,348, filed on Jan. 19, 2011.

(51) Int. Cl.
    *A61F 5/44* (2006.01)
    *A61F 13/02* (2006.01)
    *A61M 1/00* (2006.01)

(52) U.S. Cl. ........ 604/344; 604/264; 604/307; 604/317; 604/318; 604/327; 604/332; 604/333; 604/335; 604/336; 604/337; 604/338; 604/339; 604/340; 604/341; 604/342; 604/343; 604/345; 604/355; 604/356; 604/393; 604/394

(58) Field of Classification Search .................. 604/264, 604/307, 317–318, 327, 332–333, 335–345, 604/355–356, 393–394
See application file for complete search history.

(56) References Cited

U.S. PATENT DOCUMENTS

| | | | |
|---|---|---|---|
| 2,815,883 A | 12/1957 | Robins et al. | |
| 4,252,120 A | 2/1981 | Carpenter | |
| 4,439,191 A | 3/1984 | Hogan | |
| 4,705,512 A | 11/1987 | Faucher | |
| 4,790,833 A | 12/1988 | Schmidt | |
| 4,983,171 A | 1/1991 | Schirmer | |
| 5,026,362 A | 6/1991 | Willett | |
| 5,370,638 A | 12/1994 | Keyes | |
| 5,470,624 A | 11/1995 | Oreglia | |
| 5,607,412 A | 3/1997 | Brown | |
| 5,759,180 A | 6/1998 | Myhres | |
| 5,843,054 A | 12/1998 | Honig | |
| 5,865,819 A * | 2/1999 | Cisko et al. | 604/339 |
| 6,652,496 B2 | 11/2003 | Bateman | |
| 6,863,663 B1 | 3/2005 | Mills | |
| 6,966,901 B2 * | 11/2005 | Leisner et al. | 604/337 |
| D552,237 S | 10/2007 | Needham et al. | |
| 7,517,339 B2 | 4/2009 | Pedersen | |
| D624,644 S | 9/2010 | Rago | |
| 2002/0010445 A1 | 1/2002 | Gunn | |
| 2005/0127087 A1 * | 6/2005 | Clark et al. | 221/155 |
| 2005/0240163 A1 * | 10/2005 | Andersen | 604/332 |
| 2006/0258997 A1 | 11/2006 | Belt | |
| 2008/0208145 A1 | 8/2008 | McCulloch | |
| 2010/0217215 A1 * | 8/2010 | Lykke et al. | 604/344 |
| 2010/0241093 A1 | 9/2010 | Hooper | |

FOREIGN PATENT DOCUMENTS

| | | |
|---|---|---|
| EP | 0 408 296 | 1/1991 |
| EP | 2 074 973 A1 | 7/2009 |
| EP | 0 633 292 | 2/2010 |

\* cited by examiner

*Primary Examiner* — Melanie Hand
*Assistant Examiner* — Joshua Lee
(74) *Attorney, Agent, or Firm* — Charles A. Lemaire; Lemaire Patent Law Firm, P.L.L.C.

(57) ABSTRACT

The present invention is an ostomy-bag cover that provides a waterproof covering for an ostomy bag. This permits a patient wearing an ostomy bag to shower or bathe without getting his or her ostomy bag wet. In some embodiments, the ostomy-bag cover is constructed such that the patient can engage in water related activities, including swimming, while wearing the ostomy-bag cover over the ostomy bag and prevent the ostomy bag from getting wet. In some embodiments, the ostomy-bag cover includes a resealable opening configured to allow the patient to empty the ostomy bag without the need to remove the ostomy-bag cover. In other embodiments, the ostomy-bag cover includes a waterproof exhaust vent to allow air to be removed from the ostomy-bag cover.

26 Claims, 20 Drawing Sheets

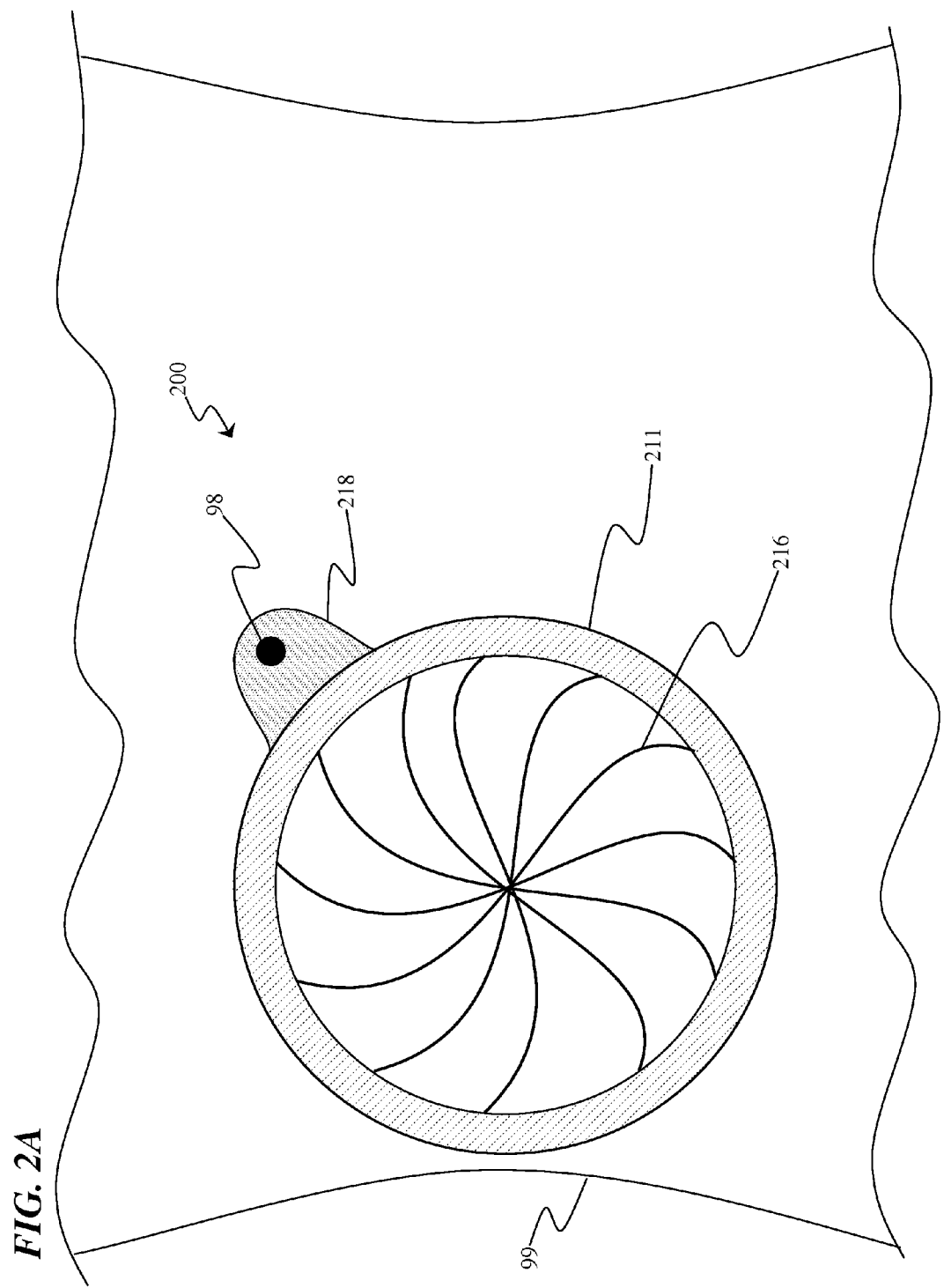

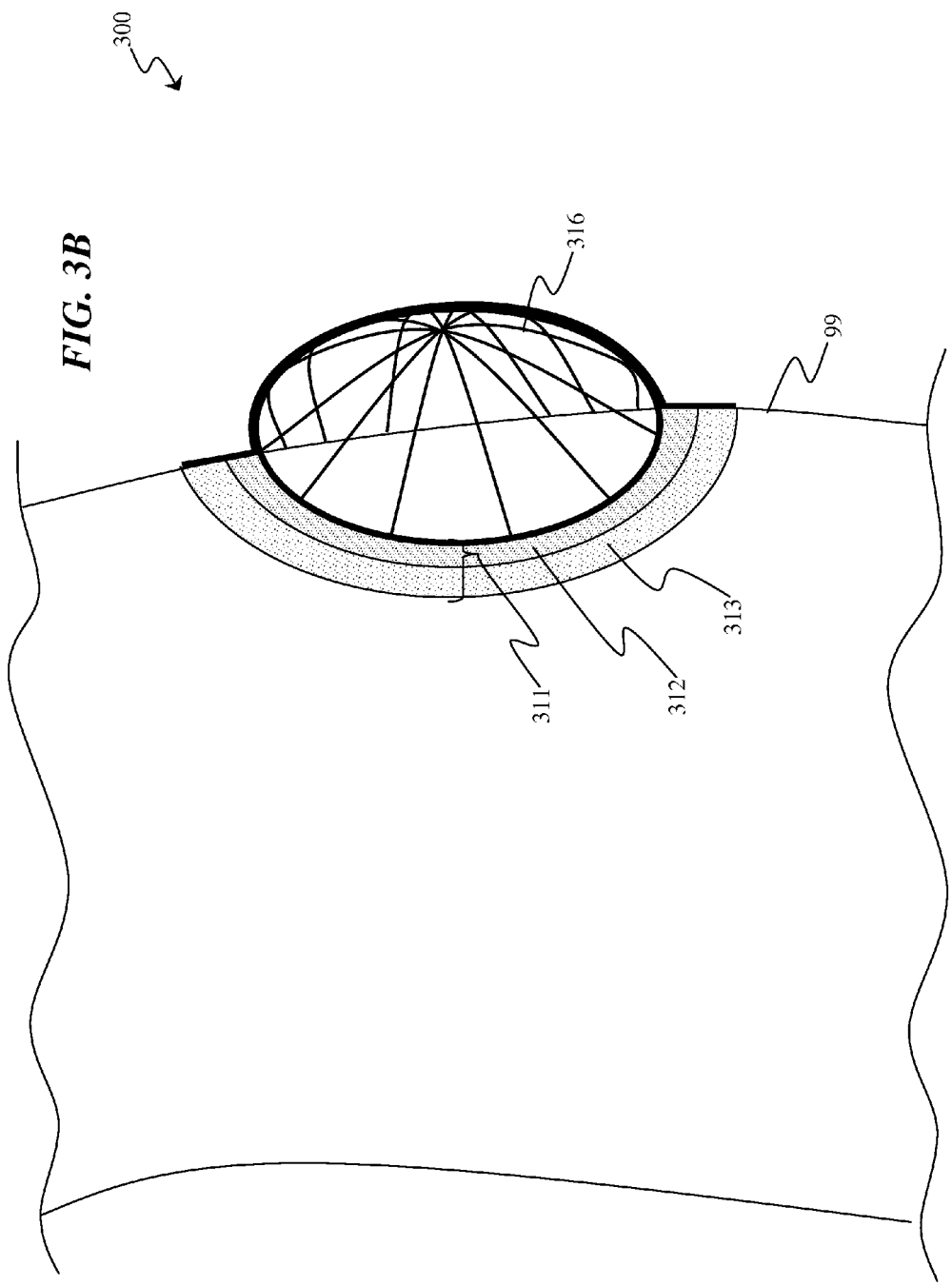

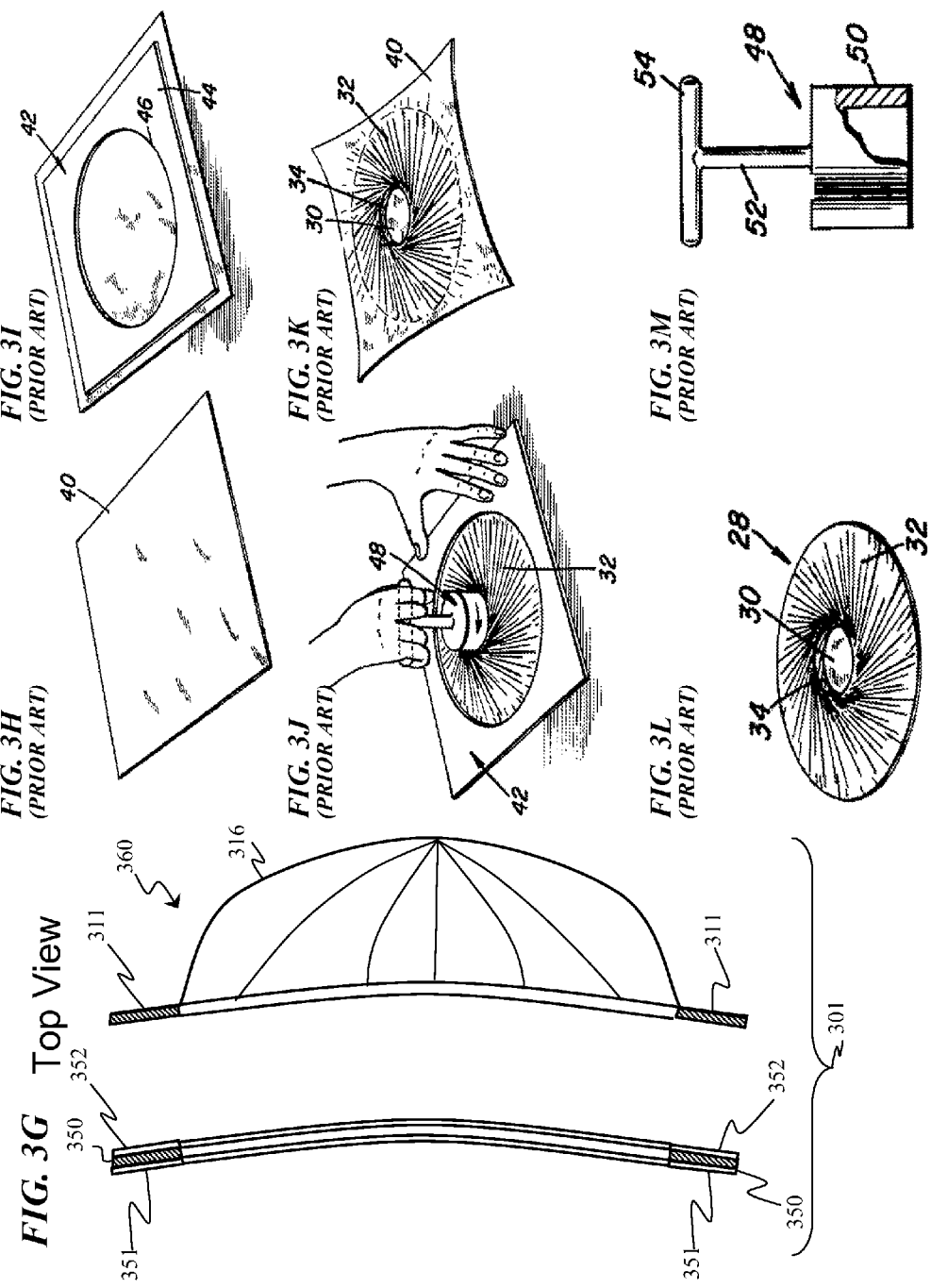

OSTOMY BAG WATERPROOF COVER AND METHOD

CROSS-REFERENCE TO RELATED APPLICATIONS

This invention claims the benefit of and priority to U.S. Provisional Patent Application 61/434,348 entitled "OSTOMY BAG WATERPROOF COVER AND METHOD" filed Jan. 19, 2011, which is hereby incorporated by reference in its entirety.

FIELD OF THE INVENTION

The invention relates generally to ostomy bags and, more specifically, to covers for ostomy bags that can protect an ostomy bag during bathing or other activities.

BACKGROUND OF THE INVENTION

An ostomy is a surgical procedure in which an opening is created in a body for the discharge of waste. In this procedure, a passageway or stoma is made, typically through the abdominal wall and skin of the patient, and a portion of an intestine is surgically connected to the stoma so that waste matter can exit the body.

As used herein, "ostomy" is intended to cover all types surgical procedures in which a stoma is formed through the skin and is connected to an internal organ. Two common ostomies are "colostomy" wherein the colon is connected to the stoma, and "ileostomy" wherein the small intestine is connected to the stoma. Waste matter (fecal material) is uncontrollably discharged from the stoma. Consequently, the patient is required to wear an ostomy appliance, commonly known as an ostomy bag (or a stoma bag), wherein a flange of the ostomy bag is attached to the abdominal wall of the patient with an adhesive, and a plastic waste bag attached to the flange collects the waste discharged by the body. In some embodiments, the plastic waste bag can be removed from the flange and emptied as needed. A wide variety of ostomy bags are in general use.

While ostomy bags effectively collect waste matter, they present a number of problems. The actual collection bags are typically made of a plastic material that is somewhat transparent, which allows the collected waste matter in the bag to be partially visible, and which also has a tendency to stick to the body of the patient and to irritate the patient's skin. Ostomy bag covers have been designed to address these modesty and discomfort problems.

U.S. Pat. No. 4,439,191, which issued to Hogan Mar. 27, 1984 titled "Ostomy bag cover," is incorporated herein by reference. Hogan describes an ostomy bag cover for an ostomy bag of the type having an inlet, a connecting member for connecting the inlet in communication with a stoma on a wearer's body and a closeable outlet at the bottom of the ostomy bag for emptying the contents therefrom. The cover is in the form of a hollow body and includes a first aperture formed therein adapted to be disposed in registry with the inlet of the ostomy bag and to receive the connecting member therethrough. A second aperture is formed in the bottom of the hollow body between spaced side portions thereof and is adapted to be disposed in proximity with the outlet of the ostomy bag. A releasable fastener is mounted on the space sides for releasably closing the second aperture in the hollow body.

U.S. Pat. No. 4,983,171, which issued to Schirmer Jan. 8, 1991 titled "Comfortable ostomy pouch," is incorporated herein by reference. Schirmer describes an ostomy bag that is made with air cushion film so that the air bubbles are on the bag outside. Air cushion film is known as bubblepak in the industry. The bubbles afford a high degree of comfort to the person wearing the ostomy bag.

U.S. Pat. No. 5,026,362, which issued to Willett Jun. 25, 1991 titled "Ostomy bag holder and cover," is incorporated herein by reference. Willett describes an ostomy bag holder and cover of lightweight fabric material, comprises a waist encircling belt adapted to be adjustably secured about the waist of the user, and a pouch secured to the belt for holding and covering an ostomy bag, said pouch comprising a back panel having a cut-out therein for providing access from an ostomy bag to a stoma, and a front panel having releasable fastening means thereon for releasably attaching the front panel to the belt for covering an ostomy bag supported in the pouch. The front and back panels define a pocket at their lower ends for supporting the ostomy bag.

U.S. Pat. No. 5,607,412, which issued to Brown Mar. 4, 1997 titled "Ostomy bag cover," is incorporated herein by reference. Brown describes an ostomy bag cover that is formed of a single piece of a soft knit fabric, folded and sewn so that there are no rough edges in contact with the patient. The cover contains the ostomy bag and isolates the patient from direct contact of the plastic bag with the skin. The cover has a distal side panel and left and right proximal side panels that meet at a vertical midline on the patient side of the cover. The panels are left detached from one another from the top seam partway down the midline to define a vertical slot through which the fitting or flange of the ostomy bag protrudes. Another slot is provided along the bottom seam to accommodate a drain tube.

U.S. Pat. No. 5,759,180, which issued to Myhres Jun. 2, 1998 titled "Ostomy bag cover and assembly," is incorporated herein by reference. Myhres describes a cover for an ostomy bag which is opaque to camouflage waste in the ostomy bag. The cover is also moisture resistant to prevent the deterioration of the cover when exposed to moisture as well as to prevent the cover from separating from an ostomy bag when exposed to moisture. The cover may also include decorative patterns. The cover comprises a body portion and a neck portion. The body portion is shaped to substantially cover a body portion of a front side of an ostomy bag. The neck portion is shaped to substantially cover at least a lower part of a neck portion of a front side of an ostomy bag.

U.S. Pat. No. 5,843,054, which issued to Honig Dec. 1, 1998 titled "Ostomy bag cover," is incorporated herein by reference. Honig describes an ostomy bag cover for an ostomy bag of the type having an inlet, a connecting member for connecting the inlet in communication with a stoma on a wearer's body and a closable outlet at the bottom of the ostomy bag for emptying the contents therefrom. The cover is in the form of a hollow body and includes a ribbed aperture formed therein adapted to be disposed in close tolerance with the inlet of the ostomy bag and to receive the connecting member therethrough. Said ribbed aperture provides an improved fit of the ostomy bag cover in relation to the ostomy bag inlet thereby providing the wearer with greater comfort by reduced contact of the wearer's skin with the ostomy bag, the connecting member, or the ostomy inlet. A second aperture is formed in the bottom of the hollow body between spaced side portions thereof and is adapted to be disposed in proximity with the outlet of the ostomy bag. A releasable fastener is mounted on the space sides for releasably closing the second aperture in the hollow body.

United States Patent Application 2002/0010445 by Gunn filed Jul. 19, 2001 titled "Ostomy bag cover" is incorporated herein by reference. Gunn describes an ostomy bag cover for containing within an ostomy bag. The cover has a distal panel and a proximal panel with an optional belt attachment. The two panels are of similar size and shape and are placed together and joined, as by sewing for example, along their perimeters. However, the two (2) joined panels, forming a cover, have an opening at top for accepting the ostomy bag and an opening along the bottom, for emptying the ostomy bag.

United States Patent Application 2008/0208145 by McCulloch filed Feb. 26, 2007 titled "Disposable Shower Guard for Renal Access Catheter" is incorporated herein by reference. McCulloch describes a hemodialysis catheter, also know as a renal dialysis access catheter penetrates a patients skin at an entrance site which is protected by associated bandaging, all of which needs to be protected from water when the patient takes a shower. The single use, disposable shower guard surrounds and encloses the catheter, the entrance site and the associated protective bandaging. A generally rectangular cutout in the guard is sized and oriented to surround the protective bandaging and leave a margin between the edge of the cutout and the protective bandaging so that the bandaging will not be disturbed when the guard is removed.

U.S. Pat. No. 2,815,883, which issued to Robins et al. Dec. 10, 1957 titled "Spirally Wound Covering For Popcorn Containers," is incorporated herein by reference. Robins et al. describes a cover for packages which is so constructed whereby it occupies a relatively small space when placed on a container and will open to greatly increase the effective size of the container. Robins et al. describe, in relation to prior-art FIGS. 3H to 3M, as follows: Referring now to prior-art FIGS. 3H through 3M, inclusive, it will be seen that there is illustrated the steps in forming the cover 28. Initially the cover 23 is in the form of a flat sheet of material 40 which is preferably square and formed of aluminum fob, although other desired materials may be utilized. In order to shape the cover 28 to meet the shape of the container 12 and at the same time to hold the sheet 40 in place during the cover forming operation, there is provided a pattern forming retainer 42. The retainer 42 is in the form of a flat plate. 44 which has a central circular opening 46 which is the pattern for making the cover 28. Referring now to FIG. 3M in particular, it will be seen that there is Illustrated a forming member which is referred to in general by the reference numeral 48. The forming member 48 includes an inverted cup-shaped portion 50 which has extending upwardly therefrom a shank 52. The upper end of the shank 52 terminates in a handle 54. After the pattern forming retainer 42 has been positioned as illustrated in FIG. 3i, the forming member 48 is positioned in the exact center of the opening 46. With pressure being applied simultaneously to the pattern forming retainer 42 and to the forming member 48, the forming member 48 is rotated through a slight angle. This results in the twisting of the central part of the Sheet 40 about the forming member 48, as is best illustrated in FIG. 3J. As the sheet 40 is twisted, the spiral folds 32 are simultaneously formed. Inasmuch as the folds 32 are tightly turned about the forming member 48, when the forming member 48 is lifted from its position in FIG. 3J, the central portion 30 is pulled upwardly out of the plane of the outer part of the sheet 40. Thus, when the pattern forming retainer 42 has been removed, the central portion of the sheet 40 which will become the cover 28 is slightly upwardly bowed. After the pattern forming retainer 42 has been removed from the sheet 40, a suitable die (not shown) is utilized to cut the cover 28 of a size to fit from the sheet 40.

There is a need for an improved ostomy bag cover.

BRIEF SUMMARY OF THE INVENTION

An apparatus for covering an ostomy bag of a patient, the ostomy bag having an ostomy-bag flange, wherein the ostomy-bag flange adheres to the patient's skin surrounding a stoma. In some embodiments, this apparatus includes an ostomy-bag cover, wherein the ostomy-bag cover covers the ostomy bag and its ostomy-bag flange in order to prevent water from reaching the ostomy bag and its ostomy-bag flange. The ostomy-bag cover includes a body formed from a liquid-impermeable membrane, the body having a proximal end opening and a distal end opening; a cover-flange portion connected to the proximal end opening of the body, the cover-flange portion having a patient-skin-contact side and a distal side, wherein the patient-skin-contact side has a pressure-sensitive adhesive that releasably attaches the proximal side of the flange to the patient's skin surrounding the ostomy-bag flange and forms a water-tight seal to an area of the patient's skin that surrounds the ostomy-bag-flange; and a one-way exhaust vent, wherein the vent is operable to remove excess air within the ostomy-bag cover while the cover-flange portion is sealed to the patient's skin, wherein the vent prevents water from entering the ostomy-bag cover, whereby the ostomy-bag cover forms a water-tight cover over the ostomy bag and its ostomy-bag flange In some embodiments, the present invention provides an apparatus for covering an ostomy bag of a patient, where the ostomy bag has an ostomy-bag flange, and the ostomy-bag flange adheres to the patient's skin surrounding a patient's stoma. In some embodiments, the apparatus includes an ostomy-bag cover, such that the ostomy-bag cover covers the ostomy bag and its ostomy-bag flange in order to prevent water from reaching the ostomy bag and its ostomy-bag flange. The ostomy-bag cover includes a body formed from a liquid-impermeable membrane, the body having a proximal end opening and a distal end opening. In some embodiments, the present invention further includes a cover-flange portion connected to the proximal end opening of the body of the ostomy-bag cover, where the cover-flange portion has a patient-skin-contact side (proximal side) and a distal side, and where the patient-skin-contact side has a pressure-sensitive adhesive that releasably attaches the proximal side of the flange to the patient's skin surrounding the ostomy-bag flange and forms a watertight seal to an area of the patient's skin that surrounds the ostomy-bag-flange. In some embodiments, the present invention further includes a sealable exhaust vent, such that the vent is operable to remove excess air within the ostomy-bag cover while the cover-flange portion is sealed to the patient's skin, and where the vent prevents water from entering the ostomy-bag cover, in order that the ostomy-bag cover forms a watertight cover over the ostomy bag and its ostomy-bag flange.

In some embodiments, the present invention provides a method that includes making a covering for an ostomy bag of a patient, where the ostomy bag has an ostomy-bag flange, and the ostomy-bag flange adheres to the patient's skin surrounding a patient's stoma, where the ostomy-bag cover covers the ostomy bag and its ostomy-bag flange in order to restrict water from reaching the ostomy bag and its ostomy-bag flange. In some embodiments, the method includes providing a tubular body of the ostomy-bag cover made from a liquid-impermeable membrane, where the tubular body has a proximal end opening and a distal end opening, and where the ostomy-bag cover covers the ostomy bag and its ostomy-bag flange in order to prevent water from reaching the ostomy bag and its ostomy-bag flange. In some embodiments, the present invention further includes providing a cover-flange portion connected to the proximal end opening of the tubular body, where the cover-flange portion has a patient-skin-contact side (proximal side) and a distal side, where the patient-skin-contact side has a pressure-sensitive adhesive that releasably attaches the proximal side of the flange to the skin of the patient and forms a watertight seal to an area of the patient's skin that surrounds the ostomy-bag flange. In some embodiments, the present invention further includes providing a resealable opening at the distal end of the tubular body. In other embodiments, the present invention includes adhering at least a first annular region of the proximal side of the cover-flange portion of the ostomy-bag cover to a patient with pressure-sensitive adhesive forming a watertight seal to the patient's skin, where the ostomy-bag cover forms a substantially waterproof cover over the ostomy bag and its ostomy-bag flange, and sealing the resealable opening to prevent water from entering the ostomy-bag cover.

In some embodiments, the present invention provides an apparatus for covering an ostomy bag of a patient, where the ostomy bag has an ostomy-bag flange, and where the ostomy-bag flange adheres to the patient's skin surrounding a stoma. In some embodiments, the apparatus includes a protective film means for covering the ostomy bag and its ostomy-bag flange in order to prevent water from reaching the ostomy bag and its ostomy-bag flange, where the cover (protective film means) is formed from a polymer film. In some embodiments, the present invention further includes a pressure-sensitive adhesive flange means for attaching the protective film means to a patient, where the pressure-sensitive adhesive flange means connects with the protective film means and releasably fastens the flange to the patient's skin surrounding the ostomy-bag flange and forms a water-resistant seal to the patient's skin. In other embodiments, the pressure-sensitive adhesive flange means contains an opening that is large enough for the flange to surround the ostomy-bag-flange without contacting the ostomy-bag-flange. In some embodiments, the present invention further includes a folding means for flattening (such as shown in FIGS. 3H through 3M) the protective film means and pressure-sensitive adhesive flange means for distribution, such that the protective film means and pressure-sensitive adhesive flange means are substantially flat before use and where the protective film means unfolds to fit over the ostomy bag and its ostomy-bag flange.

In some embodiments, the present invention provides an apparatus kit for covering an ostomy bag of a patient, where the ostomy bag has an ostomy-bag flange, and where the ostomy-bag flange adheres to the patient's skin surrounding a stoma. In some embodiments, the apparatus kit includes an ostomy-bag-cover body, where the ostomy-bag-cover body includes a protective covering formed from a liquid-impermeable membrane, wherein the protective covering is substantially flat before use, and wherein the protective covering unfolds to fit over the ostomy bag and its ostomy-bag flange, and the ostomy-bag-cover body further includes a cover-flange portion connected to the protective covering. These embodiments of the present invention also include an adhesive-attachment band, where the adhesive-attachment band has a first surface coated with a pressure-sensitive adhesive, and a second surface coated with a pressure-sensitive adhesive, and where the adhesive-attachment band is shaped approximately the same as the cover-flange. The pressure-sensitive adhesive on the first side of the adhesive-attachment band is covered by a first removable piece of release film, and the pressure-sensitive adhesive on the second side of the adhesive-attachment band is covered by a second removable piece of release film. The adhesive-attachment band releasably attaches the cover-flange to an area of the patient's skin surrounding the ostomy-bag flange and forms a watertight seal to an area of the patient's skin that surrounds the ostomy-bag-flange.

BRIEF DESCRIPTION OF THE FIGURES

Each of the items shown in the following brief description of the drawings represents one or more aspects of some embodiments of the present invention.

FIG. 2A is a front perspective view of an ostomy-bag-cover system 200, according to other embodiments of the present invention.

FIG. 3B is a side perspective view of an ostomy-bag-cover system 300, according to other embodiments of the present invention.

FIG. 3G is a top cross-sectional view of an ostomy-bag-cover system 301, according to other embodiments of the present invention.

FIG. 3H is a perspective view of a sheet from which the cover is formed.

FIG. 3I is a perspective view showing a pattern forming retainer positioned on the sheet as a first step in making the cover.

FIG. 3J is a perspective view showing a forming member engaged with the center of the sheet in the center of the pattern, the forming member having been twisted about its axis to produce the spiral folds in the sheet.

FIG. 3K is a perspective view of the sheet showing it after the spiral folds have been formed therein.

FIG. 3L is a perspective view of the cover after it has been cut from the sheet.

FIG. 3M is an enlarged elevational view of the forming member with a portion thereof broken away in order to clearly illustrate the details thereof.

DETAILED DESCRIPTION OF THE INVENTION

Figure 1A:
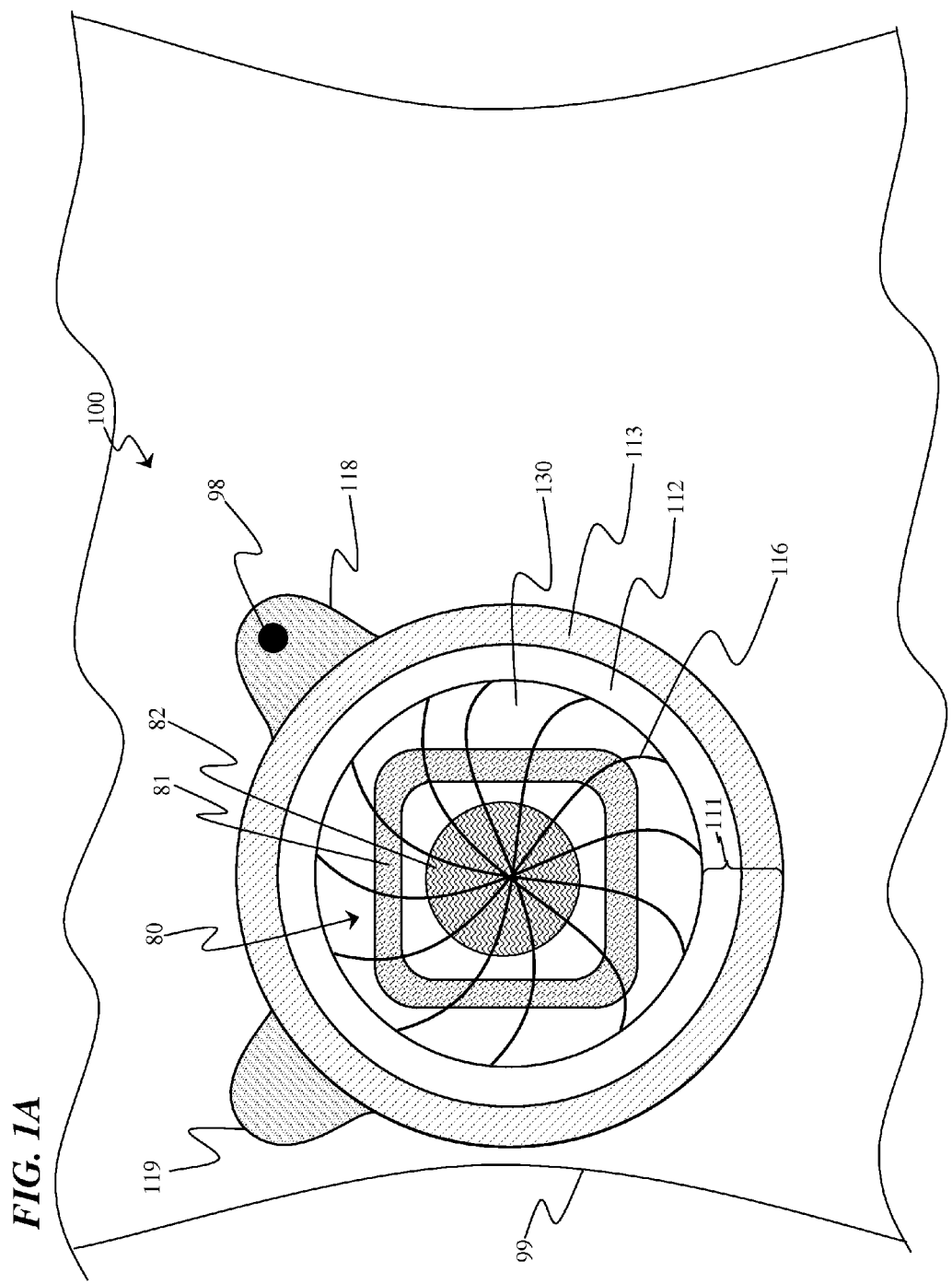
FIG. 1A is a front perspective view of an ostomy-bag-cover system 100, according to some embodiments of the present invention.

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

As used herein, the term "ostomy appliance," the term "ostomy bag" and the term "stoma bag" are synonymous. As noted above, an ostomy bag typically has a flange that is attached to the abdominal wall of the patient with an adhesive, and a plastic waste bag, attached to the flange, that collects the waste discharged by the body. In some embodiments, the plastic waste bag can be removed from the flange and emptied as needed, and then reattached to the flange for reuse.

As used herein, the term "waterproof" means keeping an item completely dry for a period of at least 60 minutes while submerged in water or exposed to water spray. As used herein, the term "watertight" means keeping an item dry for at least at least 30 minutes while exposed to water spray and at least 5 minutes while submerged in water. As used herein, the term "water-resistant" means keeping an item dry for at least 15 minutes while exposed to casual water contact, such as water spray in a shower.

As used herein, the term "band" means the substantially flat area of material between two geometric shapes, such as the area of material between two substantially concentric circles (also known as an annulus), the area of material between two substantially concentric ovals, the area between two substantially concentric rectangles, the area of material between two substantially concentric rectangles with rounded corners, the area of material between a circle/oval and a square/rounded square, or between any two geometric shapes where the inner shape is the edge of the material that surrounds an opening and the outer shape is the other outside edge of the material that surrounds the inner shape. The term "band" also includes the flat area of material between two geometric shapes where the shapes are not substantially concentric such as is the case when one side of the band is wider than another side of the band (i.e., wherein the opening is not centered within the material).

Problems are encountered with ostomy bag usage when showering. A person can do any of several things with the ostomy bag when he or she showers: the patient can wear the ostomy bag, getting it wet. The ostomy bag needs to be dried or changed after the shower to prevent moisture against the skin, causing possible chafing and skin irritation. Persons can use a hair dryer to dry the external bag. The hot air from the hair dryer causes the ostomy-bag flange adhesive as well as the fabric of the bag to wear out prematurely. Some people wash and dry the original stoma bag for reuse.

A person can remove the bag before the shower. If the person chooses to use nothing as a bag, then the excrement can flow freely during the shower and is messy and unsanitary.

In some embodiments, the present invention includes a one-piece waterproof impermeable stoma-bag cover with a flange. The impermeable plastic stoma-bag cover encloses the fabric stoma bag and the stoma bag's flange, and the flange of the stoma-bag cover is adhesively attached to the skin surrounding the flange of the stoma bag. The impermeable stoma-bag cover fits over the various styles of stoma bags and their flanges. In some embodiments, the impermeable stoma-bag cover and the cover's flange form a single unit that comes in two sizes, one for children and one for adults. After showering, the person typically removes and disposes the impermeable cover and flange. The impermeable stoma-bag cover of the present invention, with its flange, is convenient and efficient to use. Use of the stoma-bag cover minimizes the time it takes the person having a stoma bag to get ready after showering (since it is not necessary to change or dry the original stoma bag and flange); minimizes wear and tear and extends the life of the original stoma bag and its flange because it is no longer necessary to dry the original stoma bag and flange. The stoma-bag cover keeps the stoma bag dry. Use of the stoma-bag cover allows less frequent changing of the original stoma and flange, which reduces chance of skin irritation. Use of the stoma-bag cover removes some of the risk of a possible leakage that can happen when water or heat are used on the stoma bag's flange.

In other embodiments, the present invention includes a water-impermeable cover. The water-impermeable cover has a non-irritating adhesive around the open circle on the back side which adheres to the left or right side of abdomen. In some embodiments, the water-impermeable cover has optional flaps along sides to be placed over the navel (umbilicus). This is to be used if the edge of the impermeable bag ends up close to the navel, in that case the flap is put over the navel to seal off any chances of water getting into the navel and then leaking into the bag. If a person does not need the flap, the flap can be cut off.

In some embodiments, the present invention includes a waterproof cover that surrounds the ostomy bag as well as the ostomy bag's flange in one easy step, wherein the cover is a one-piece bag and adhesive flange. Attributes of the cover include:

A. One doesn't have to change stoma bags and flanges as often because the water proof bag keeps it all dry. The appliance (stoma bag) lasts longer when the flange does not get wet.

B. One doesn't have to shower without one's appliance. This eliminates having to clean up an unsanitary bathtub after a shower.

C. One saves time and there is no mess since one is not changing one's stoma appliance.

D. One will save money by not having to change one's appliance as often.

E. There will be less skin irritation due to less stoma appliance changes per week.

F. It is disposable, making it quick and easy to use and throw away.

G. It is affordable, being much less expensive than a replacement stoma bag.

H. The stoma bag flange stays dry so one doesn't have to use hairdryer to dry the stoma bag flange after showering. This saves a lot of time getting ready for the day.

I. It allows for easy, quick daily showering.

J. It is convenient.

K. It is simple to put on.

L. One doesn't have to wash the stoma bag out for reuse.

Figure 1B:
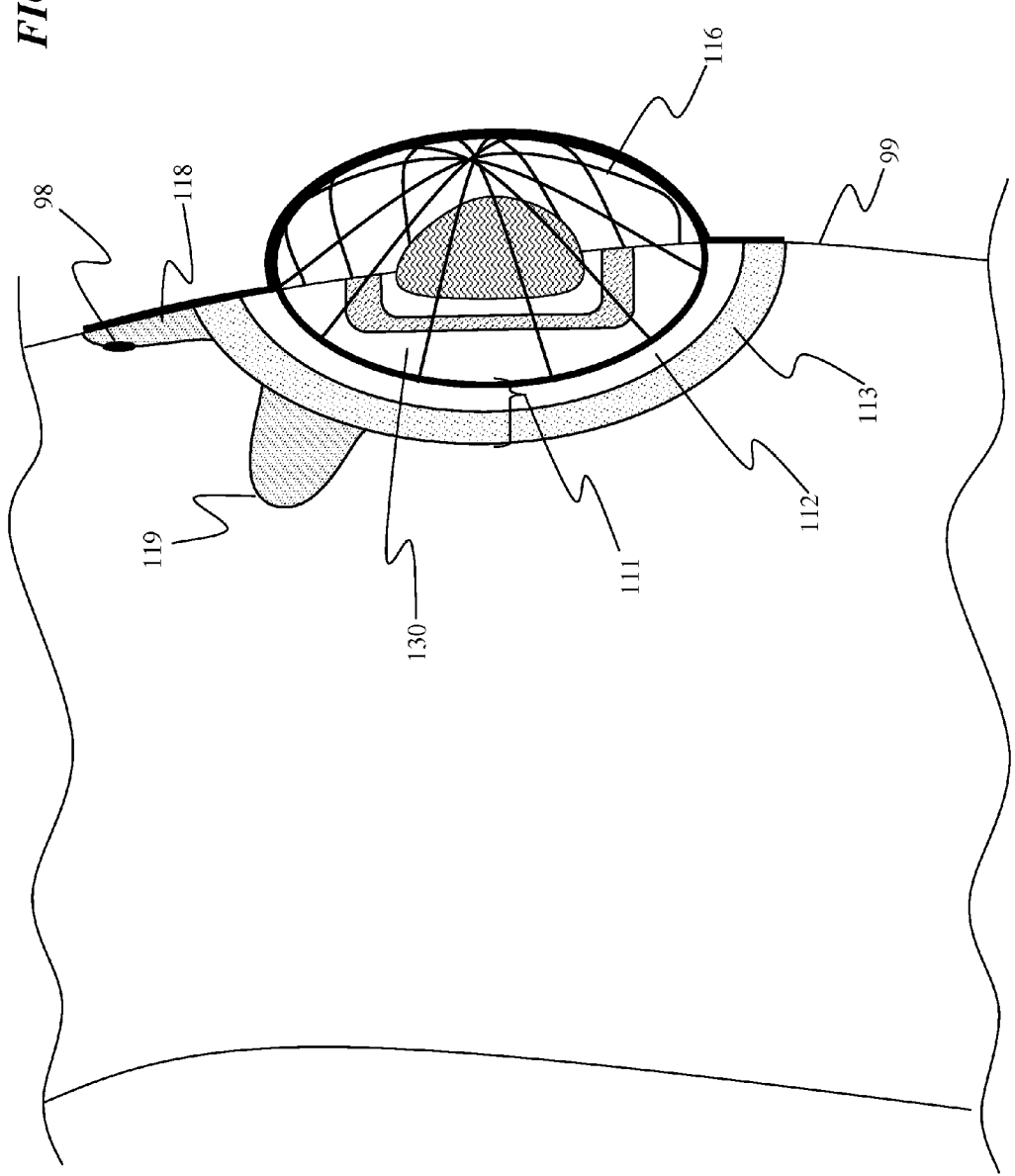
FIG. 1B is a side perspective view of an ostomy-bag-cover system 100, according to some embodiments of the present invention.

FIG. 1A is a front perspective view and FIG. 1B is a side perspective view of an ostomy-bag cover system 100, according to some embodiments of the present invention. In some embodiments, the ostomy bag cover 100 includes a flange 111 and an impermeable plastic bag cover 116. The impermeable plastic bag cover 116 is attached to the inner-portion 112 of the flange 111, and the outer portion of the proximal surface of the flange 111 is covered with a pressure-sensitive adhesive 113 that adheres to the abdomen of the patient 99. In some embodiments, the adhesive covered region of the ostomy-bag-flange 113 is 1 cm. wide. In other embodiments, the adhesive covered region of the ostomy-bag-cover flange 113 is less than 1 cm wide. In other embodiments, the adhesive covered region of the ostomy-bag-flange 113 is more than 1 cm wide.

The ostomy-bag cover covers an ostomy bag 80, wherein the ostomy bag is any of several commercially available ostomy bags. The ostomy bag typically includes a stoma flange 81 and a stoma bag 82 attached to the stoma flange and wherein a proximal surface of stoma flange 81 is covered with a pressure-sensitive adhesive that adheres to the abdomen of the patient 99. In some embodiments, the ostomy bag cover 100 includes tabs 118 and 119 used to cover the navel 98 of the patient 99 if the person's navel is near the outer portion of the ostomy bag cover flange 113. The appropriate tab is used depending of which side of the body the stoma is located, wherein, in some embodiments, the unneeded tab can be removed. In some embodiments, both tabs can be removed if neither is needed. In some embodiments, the inside opening of the ostomy bag cover flange 111 is sized large enough that an open space 130 is formed between the ostomy-bag flange 81 and the ostomy-bag-cover flange 111. When attached, the ostomy bag cover provides a water-impermeable covering for the ostomy bag, such that in some embodiments, the patient can shower while wearing the ostomy bag cover and not have the ostomy bag get wet.

Figure 2B:
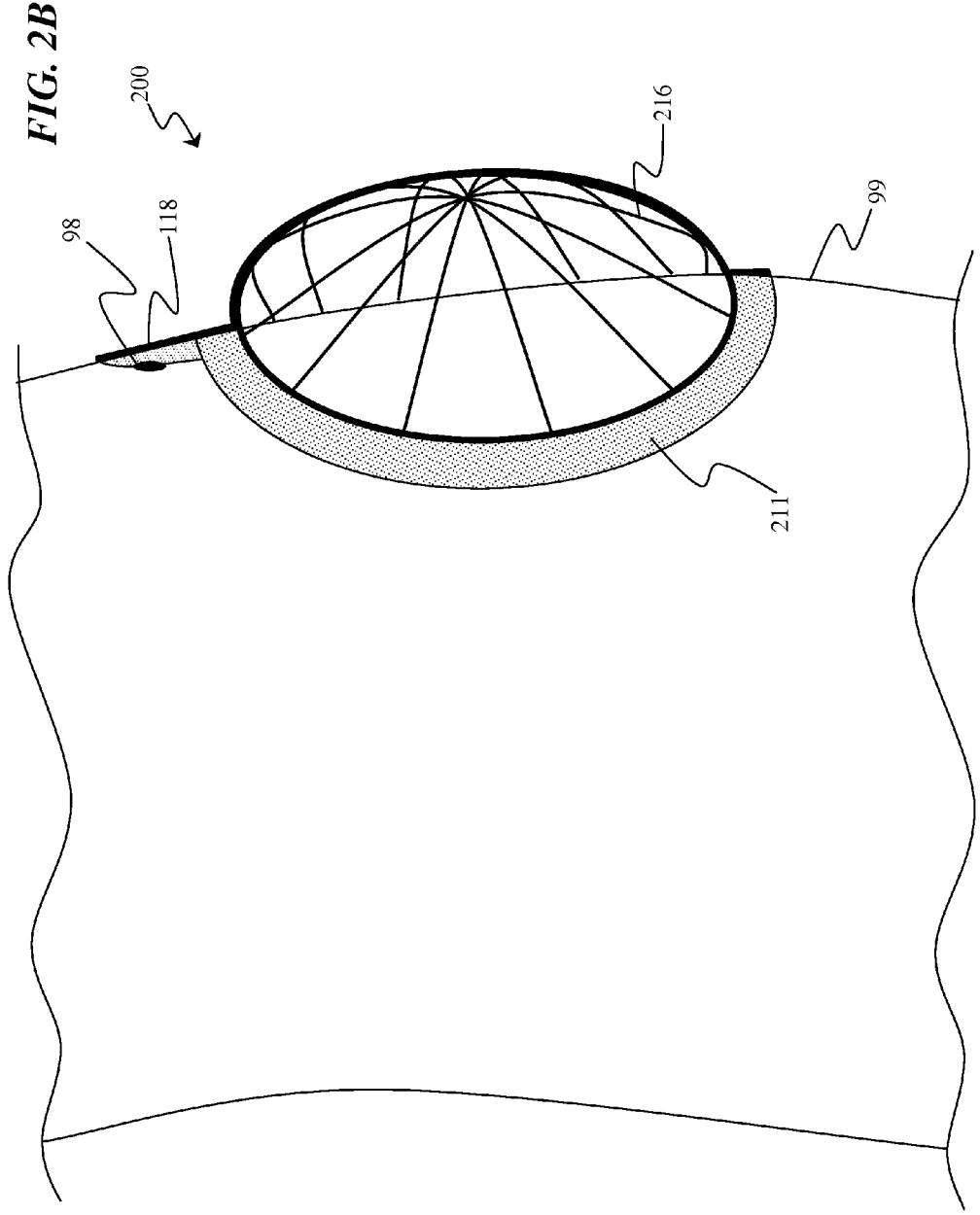
FIG. 2B is a side perspective view of an ostomy-bag-cover system 200, according to other embodiments of the present invention.

FIG. 2A is a front perspective view and FIG. 2B is a side perspective view of an ostomy-bag cover system 200, according to other embodiments of the present invention. The ostomy-bag cover 200 includes a flange 211 which is attached to a flexible plastic film cover 216. The flange 211 removeably attaches to the abdomen of the patient 99 with an adhesive on the proximal side of the flange 211 wherein the seal formed by the flange and the skin of the patient is substantially watertight. Further, in other embodiments of the present invention, a tab 218 is attached to the ostomy-bag-cover flange 211 such that the tab 218 is used to cover and seal the perimeter of the area around the navel 98 of the patient 99 when the stoma is located near the navel such that ostomy-bag-cover flange 211 may not adequately seal all of the perimeter of the area around an ostomy bag (not shown) due to the uneven surface of the skin in the proximity of the navel. If not needed, the ostomy-bag-cover tab 218 can be removed, either by cutting it off, or in some embodiments, torn along perforations at the connection of the tab and the ostomy-cover flange 211. The ostomy-bag cover 200 keeps water away from the ostomy bag (not shown) so that in some embodiments, the patient can shower or bathe without getting his or her ostomy bag wet. In some embodiments, the ostomy-bag cover is single-use, and is removed and disposed of after the patient bathes or showers.

Figure 3A:
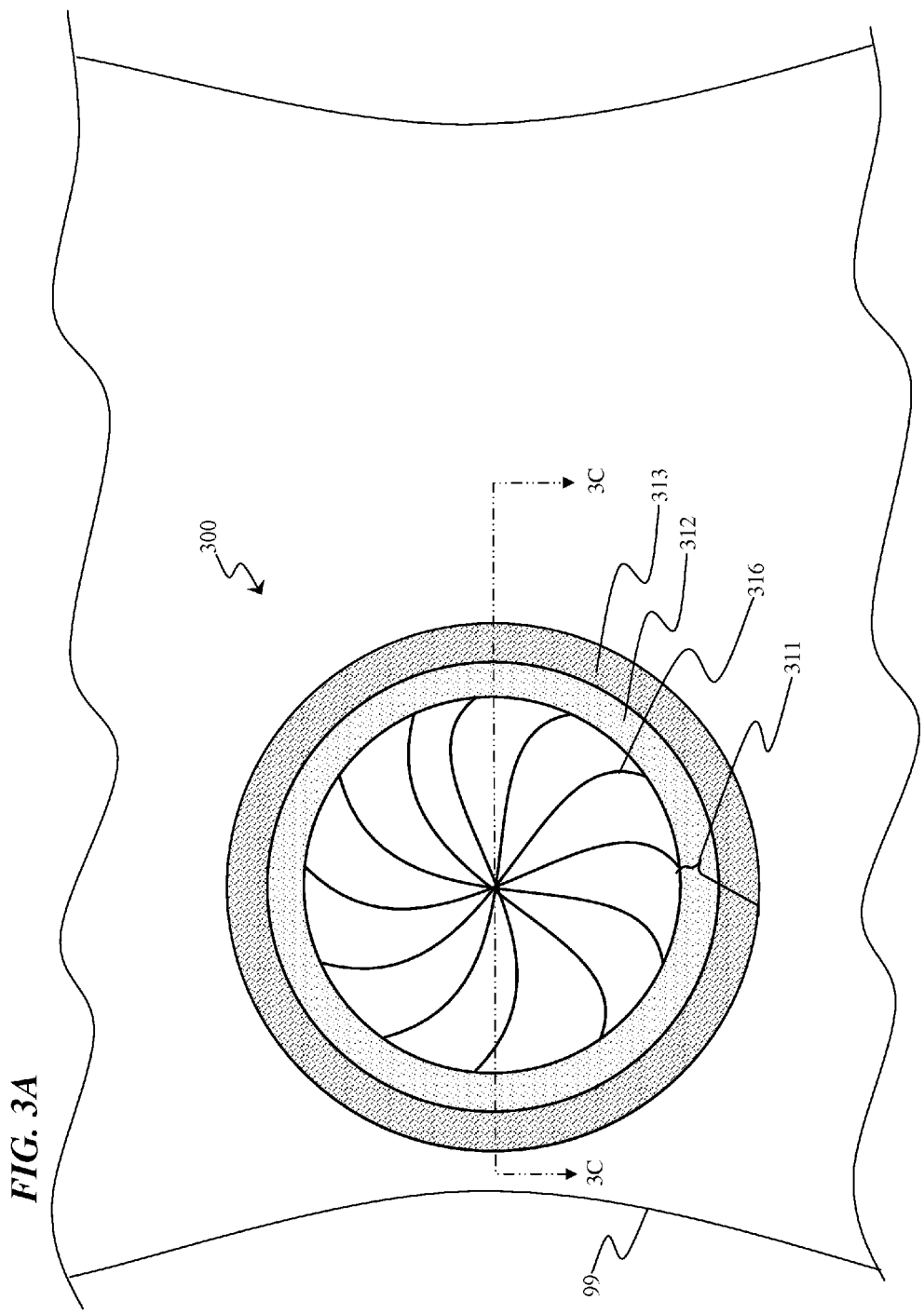
FIG. 3A is a front perspective view of an ostomy-bag-cover system 300, according to other embodiments of the present invention.

FIG. 3A is a front perspective view and FIG. 3B is a side perspective view of an ostomy-bag cover system 300, according to other embodiments of the present invention. The ostomy-bag cover 300 includes a flange 311 and a liquid-impermeable flexible cover 316. In some embodiments, the liquid-impermeable flexible cover folds flat (such as shown in FIGS. 3H through 3M) for packaging and distribution, and unfolds to cover an ostomy bag (not shown). In some embodiments, this unfolding can be similar to that used in "Jiffy Pop" package tops, as described in U.S. Pat. No. 2,815,883 to Robins et al. issued Dec. 10, 1957 titled "Spirally Wound Covering For Popcorn Containers".

In some embodiments, the ostomy-bag-cover flange 311 includes an inner region 312 and an outer region 313, wherein the flange inner region 312 is attached to the liquid-impermeable flexible cover 316 and the proximal (patient-skin) side of the flange 311 is coated with an adhesive that releasably fastens the ostomy-bag cover to the abdominal skin of the patient 99. The ostomy-bag cover when attached to the patient forms a substantially watertight covering over the ostomy bag.

Figure 3C:
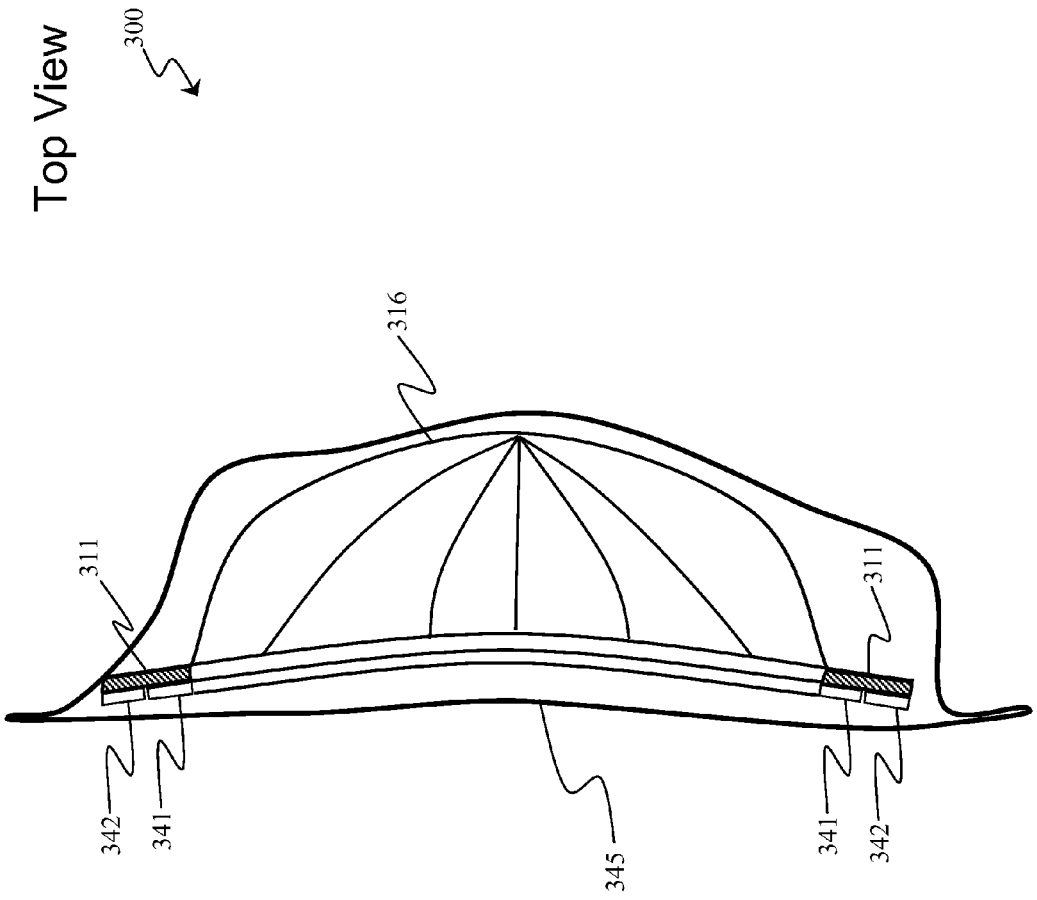
FIG. 3C is a top cross-sectional view of an ostomy-bag-cover system 300, according to other embodiments of the present invention.
Figure 3D:
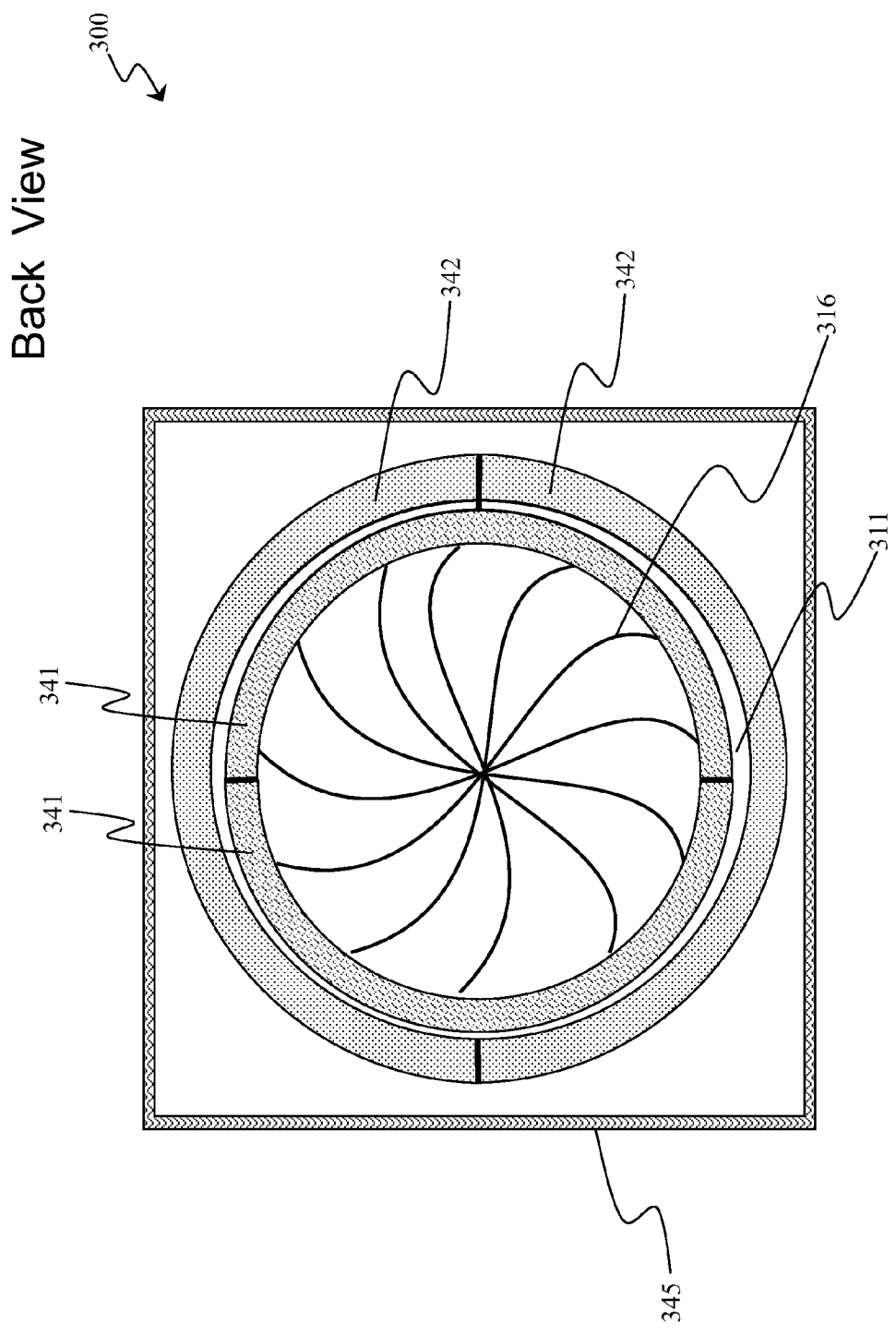
FIG. 3D is a back view of an ostomy-bag-cover system 300, according to other embodiments of the present invention.

FIG. 3C is a top cross-sectional view and FIG. 3D is a back view of the ostomy-bag-cover system 300, according to some embodiments of the present invention. In other embodiments, the ostomy-bag-cover flange 311 is coated with an adhesive that releasably fastens the ostomy-bag cover to the abdominal skin of the patient 99, forming a watertight seal between the flange 311 and the skin of the patient 99. In some embodiments, the adhesive coated flange is protected with at least one thin, easily removable layer of material during shipping to prevent the flange adhesive from adhering to anything prior to being attached to the patient's skin. In some embodiments, the protective material can be paper. In other embodiments, the protective material can be plastic or other thin film. To attach the ostomy-bag cover, the patient first removes the protective layer 341 from the inner region of the ostomy-bag-cover flange 311, and then positions the ostomy-bag cover in the desired location on his or her abdominal skin. The adhesive on the inner region of the flange holds the ostomy-bag cover to the patient's skin and aids in the positioning of the ostomy-bag cover. Once the ostomy-bag cover is positioned as desired, the protective layer 342 from the outer region of the flange 311 is removed and the flange is firmly pressed onto the patient's skin, forming a watertight seal. In the process of attaching the ostomy-bag cover, the ostomy-bag cover may have to be repositioned one or more times, or may flex in handling, resulting in wrinkles in the flange and possibly areas on the flange where the adhesive has become weak. In such cases, the needed watertight seal between the flange and the skin of the patient may be compromised. The adhesive on the outer region of the flange, which is not exposed until the ostomy-bag cover is positioned on the patient's skin, ensures a good seal between the flange and the skin. In some embodiments, each ostomy-bag cover is enclosed in its own wrapper 345 made of, e.g., paper, cardboard, plastic, foil and/or the like.

In some embodiments, each of the protective layers 341 and 342 is a single piece of material. In other embodiments, either or both of the protective layers is formed from two pieces of material as shown in FIG. 3D. This allows the layer of protective material to be more easily removed, especially the layer of protective material 342 that covers the outer region of the flange, since this layer of protective material is removed after the ostomy-bag cover is partially attached to the patient's abdominal skin with the adhesive on the inner region of the ostomy-bag-cover flange. In some embodiments of the present invention, the ostomy-bag-cover flange 311 is one centimeter wide. In other embodiments, the ostomy-bag-cover flange 311 is wider than one centimeter. In other embodiments, the ostomy-bag-cover flange 311 is narrower than one centimeter. In some embodiments, each ostomy-bag cover is enclosed in its own wrapper 345 made of, e.g., paper, cardboard, plastic, foil and/or the like.

In some embodiments, each of the protective layers 341 and 342 is a single piece of material. In other embodiments, either or both of the protective layers is formed from two pieces of material as shown in FIG. 3D. This allows the layer of protective material to be more easily removed, especially the layer of protective material 342 that covers the outer region of the flange, since this layer of protective material is removed after the ostomy-bag cover is partially attached to the patient's abdominal skin with the adhesive on the inner region of the ostomy-bag-cover flange. In some embodiments of the present invention, the ostomy-bag-cover flange 311 is one centimeter wide. In other embodiments, the ostomy-bag-cover flange 311 is wider than one centimeter. In other embodiments, the ostomy-bag-cover flange 311 is narrower than one centimeter.

The ostomy-bag cover 300 keeps water away from the ostomy bag (not shown) so that in some embodiments, the patient can shower or bathe without getting his or her ostomy bag wet. In some embodiments, the ostomy-bag cover is single-use, and is removed and disposed of after the patient bathes or showers.

In other embodiments of the present invention, only the outer protective layer 342 is removed prior to attaching the ostomy-bag cover to the abdominal skin of the patient. After showering or bathing, the patient removes the ostomy-bag cover and keeps it for a second use. For the second use of the ostomy-bag cover, the inner protective layer 341 is removed prior to attaching the ostomy-bag cover to the abdominal skin of the patient. The ostomy-bag is then removed and disposed of after the patient bathes or showers.

Figure 3E:
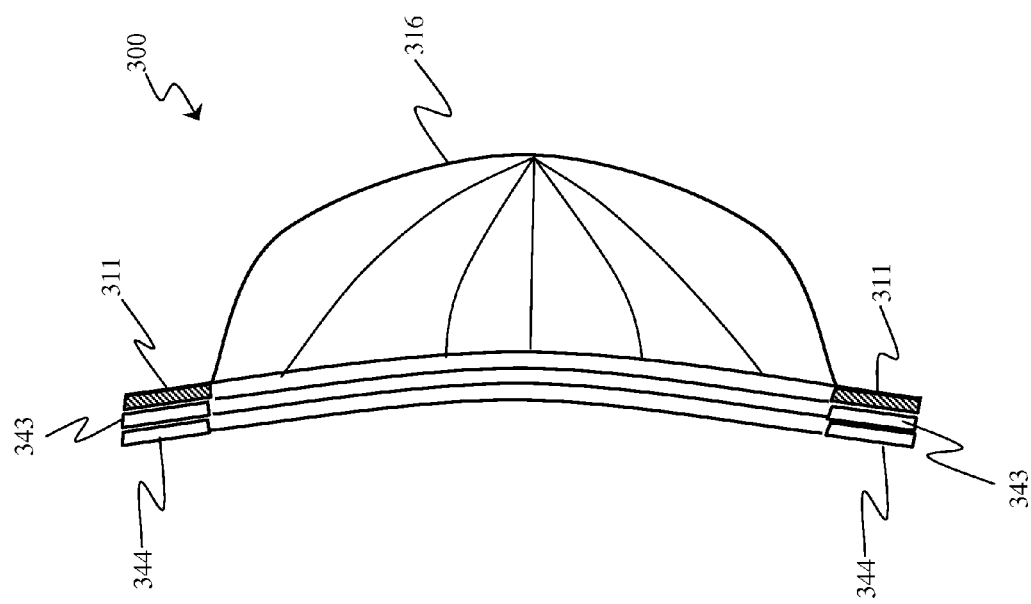
FIG. 3E is a top cross-sectional view of an ostomy-bag-cover system 300, according to other embodiments of the present invention.

FIG. 3E is a top cross-sectional view of an ostomy-bag cover system 300. In some embodiments, at least a first layer of protective material 343 and a second layer of protective material 344 cover the ostomy-bag-cover flange 311. The proximal (patient-skin) side of the flange 311 is coated with an adhesive that releasably fastens the ostomy-bag cover to the abdominal skin of the patient 99. The first layer of protective material 343 covers and protects the adhesive on the proximal (patient-skin) side of the flange 311, and the proximal side first layer of protective material 343 is coated with an adhesive that releasably fastens the ostomy-bag cover to the abdominal skin of the patient 99. The second layer of protective material 344 covers and protects the adhesive on proximal side of the first layer of protective material 343. In use, the second protective layer 344 is removed, exposing the adhesive on the proximal side of the first protective layer 343, and the ostomy-bag cover is attached to the abdominal skin of the patient. After showing or bathing, the ostomy-bag cover is removed for later reuse. For a second use, the first protective layer 343 is removed, exposing the adhesive on the proximal side of the flange 311, and the ostomy-bag cover is attached to the abdominal skin of the patient. After the second use, the ostomy bag cover can be disposed of.

Figure 3F:
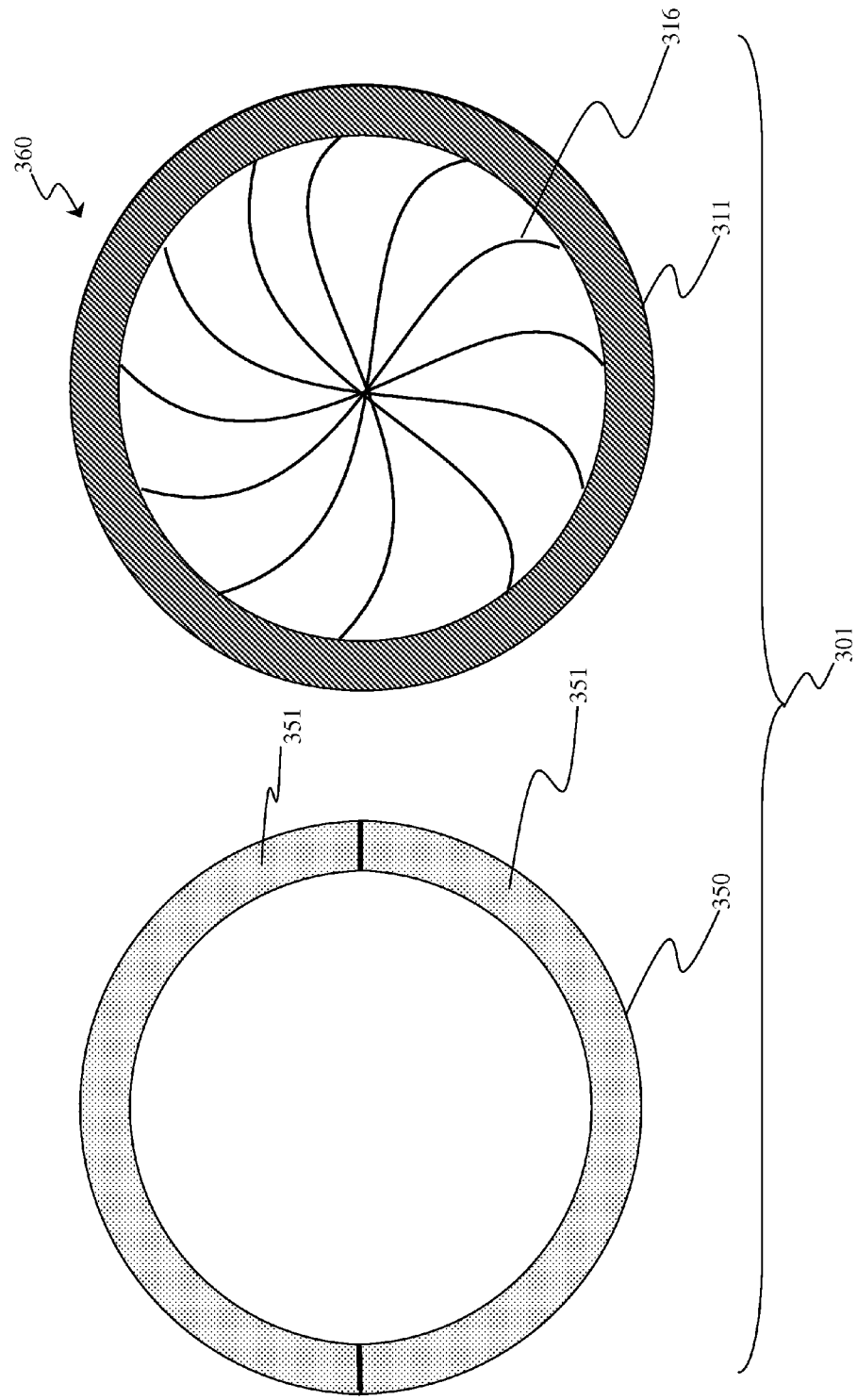
FIG. 3F is a back view of an ostomy-bag-cover system 301, according to other embodiments of the present invention.

FIG. 3F is a back view and FIG. 3G is a top cross-sectional view of an ostomy-bag cover kit 301. In some embodiments, the ostomy-bag cover kit includes an ostomy-bag cover body 360 and an adhesive-attachment band 350, wherein the adhesive-attachment band is shaped substantially the same as the ostomy-bag-cover flange 311. The adhesive-attachment band has a first surface which is coated with an adhesive and a second surface which is coated with an adhesive, and releasably fastens the ostomy-bag cover to the abdominal skin of the patient 99. A first layer of protective material 351 covers and protects the adhesive on the first surface of the adhesive-attachment band and a second layer of protective material 352 covers and protects the adhesive on the second surface of the adhesive-attachment band. In some embodiments, each of the protective layers 351 and 352 is a single piece of material. In other embodiments, either or both of the protective layers are formed from more than one piece of material as shown in FIG. 3F. In some embodiments, the adhesive-attachment band 350 is constructed from a polymer film or polymer foam. In other embodiments, the adhesive-attachment band is constructed from paper. In some embodiments, the layers of protective material 351 and 352 can be paper. In other embodiments, the layers of protective material 351 and 352 can be plastic or other thin film.

In use, the patient removes the first layer of protective material 351 from the first surface of the adhesive-attachment band 350 and places the adhesive-attachment band on his or her abdomen in the appropriate location around the ostomy-bag flange. Then the patient removes the second protective layer 352 on the second side of the adhesive-attachment band and attaches the ostomy-bag-cover flange to the adhesive-attachment band forming watertight seal between the ostomy-bag cover and the patient's skin.

Figure 4A:
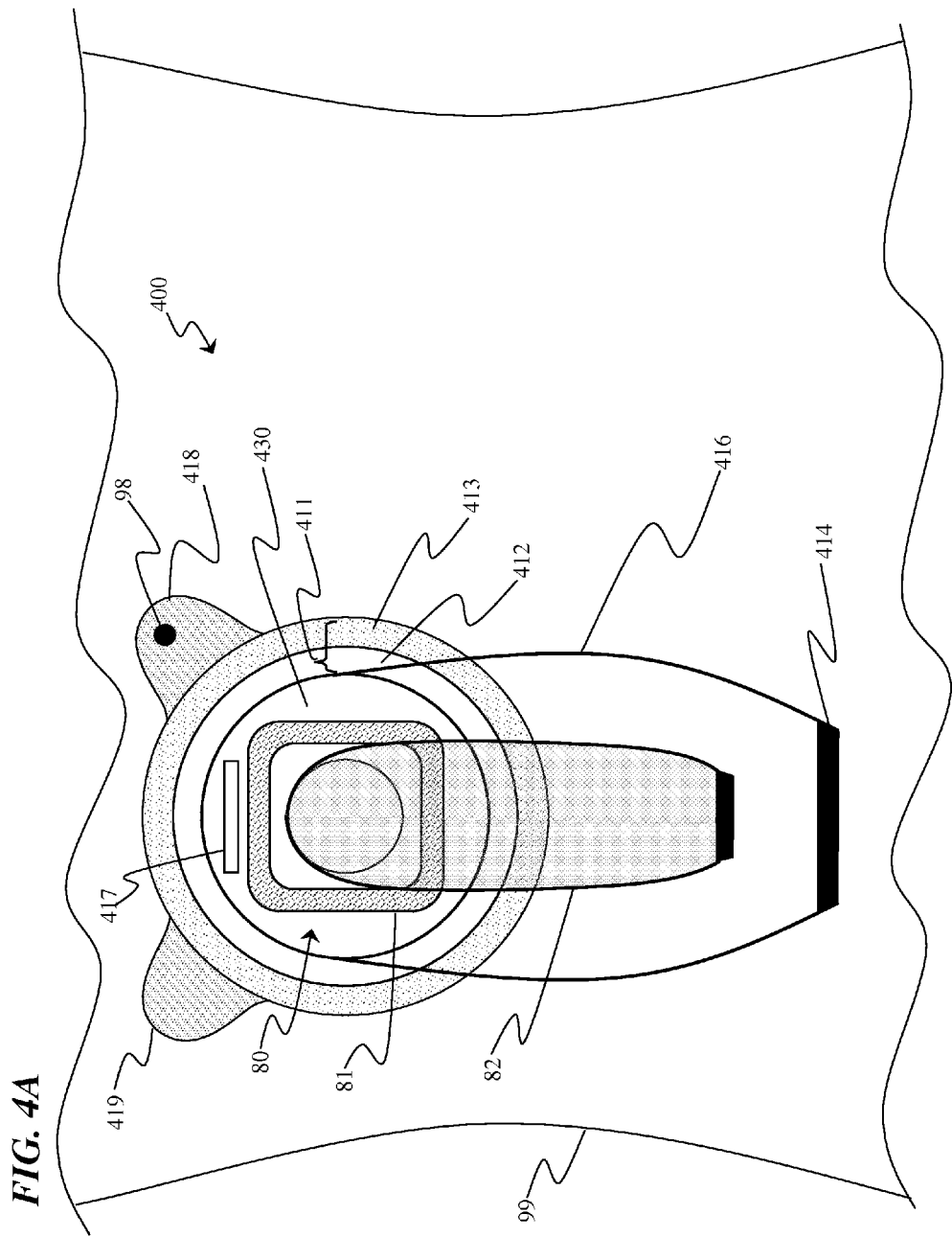
FIG. 4A is a front perspective view of an ostomy-bag-cover system 400, according to some embodiments of the present invention.
Figure 4B:
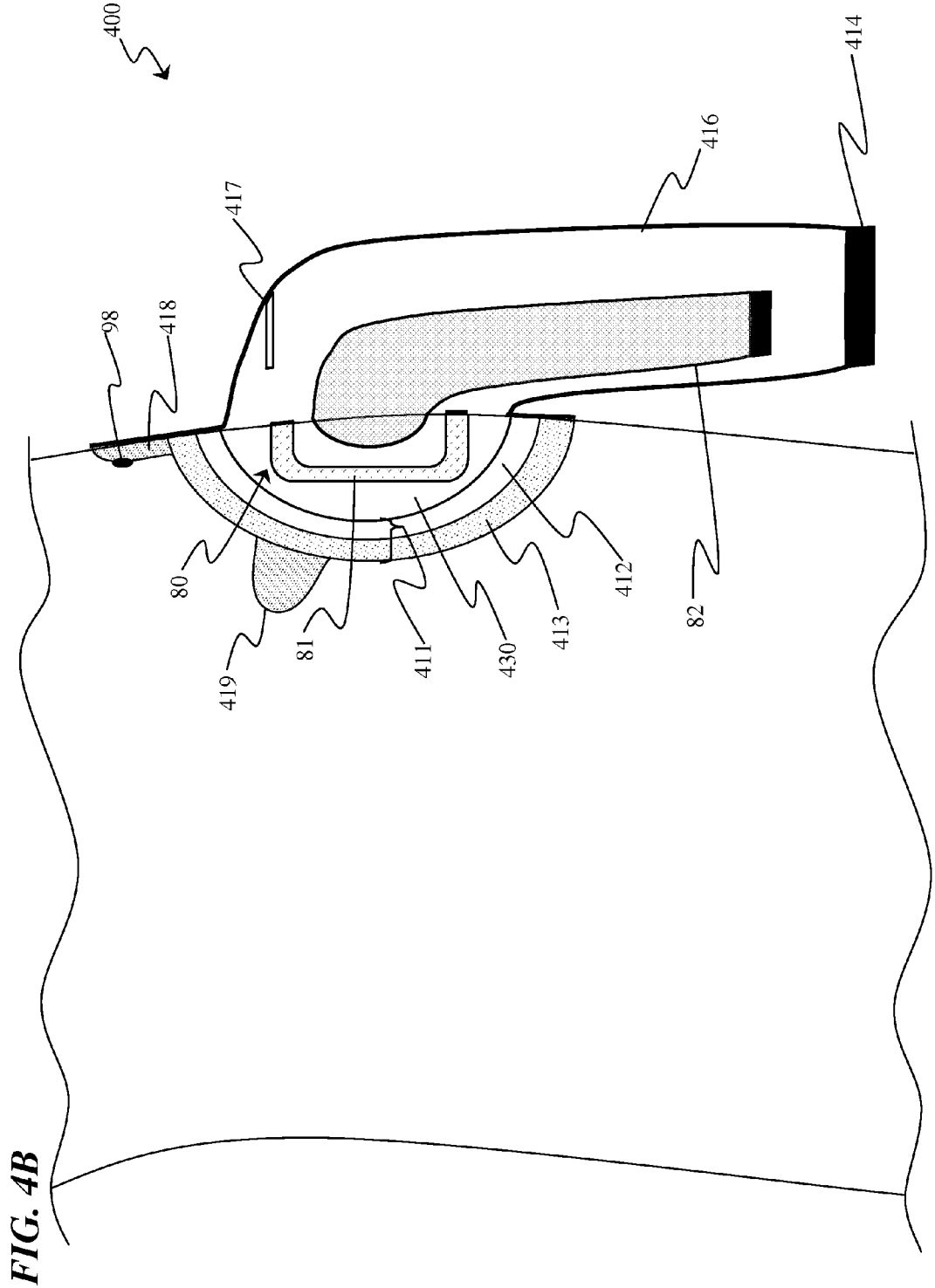
FIG. 4B is a side perspective view of an ostomy-bag-cover system 400, according to some embodiments of the present invention.

FIG. 4A is a front perspective view and FIG. 4B is a side perspective view of an ostomy-bag cover system 400, according to some embodiments of the present invention. In some embodiments, wherein the ostomy-bag cover 400 includes a flange 411 and a water impermeable plastic bag cover 416. The water impermeable plastic bag cover 416 is attached to the inner region 412 of the flange 411, and the outer region 413 of the proximal surface of the flange 411 is covered with a pressure-sensitive adhesive that adheres to the skin of the abdomen of a patient 99 forming a water resistant seal between the patient and the ostomy-bag cover. The ostomy bag 80 is any of several commercially available ostomy bags and typically includes a stoma flange 81 and a stoma bag 82 attached to the stoma flange 81, wherein a proximal surface of stoma flange 81 is covered with a pressure-sensitive adhesive that adheres to the abdomen of the patient 99. In some embodiments, the ostomy-bag-cover flange 411 is sized so that there is uncovered patient skin 430 between the ostomy-bag-cover flange 411 and the ostomy-bag flange 81. When an ostomy-bag cover is attached to a patient, the ostomy-bag cover and the adhesively formed seal result in a completely or nearly completely waterproof covering for the patient's ostomy bag. In some embodiments, the water impermeable plastic bag cover 416 includes a waterproof one-way vent 417 that allows air or other gases to be expelled from inside of the sealed ostomy-bag cover without the need to remove the ostomy-bag cover. This commonly referred to as "burping" the bag. In other embodiments, the water impermeable plastic bag cover 416 includes a watertight resealable opening 414, through which the ostomy bag 80 can be emptied without removing the ostomy-bag cover. In some embodiments, the resealable opening is a zipper-style closure such as the type found on resealable ziplock plastic bags. In other embodiments, the opening is sealed with a clip or other fastener wherein the patient can unclip and unroll bottom of waterproof bag, pull out the ostomy bag from inside, empty the ostomy bag, and then roll water impermeable plastic bag cover and clip it to reestablish the watertight seal. In other embodiments, the opening is sealed with a Velcro closure.

In some embodiments, the water impermeable material of plastic bag 416 is of sufficient strength and durability, such as a heavy gauge plastic, to permit the patient to swim with the ostomy-bag cover 400 in place, attached to the skin of his or her abdomen. This allows the patient to swim or engage in other wet activities without getting his or her ostomy bag wet.

In some embodiments, the ostomy bag cover 400 includes tabs 418 and 419 used to cover the navel of the patient 99 if the navel is an area near the outer region of the ostomy-bag-cover flange 413. The appropriate tab is used depending of which side of the body the stoma is located, wherein the unneeded tab can be removed. Both tabs can be removed if neither is needed.

Figure 5A:
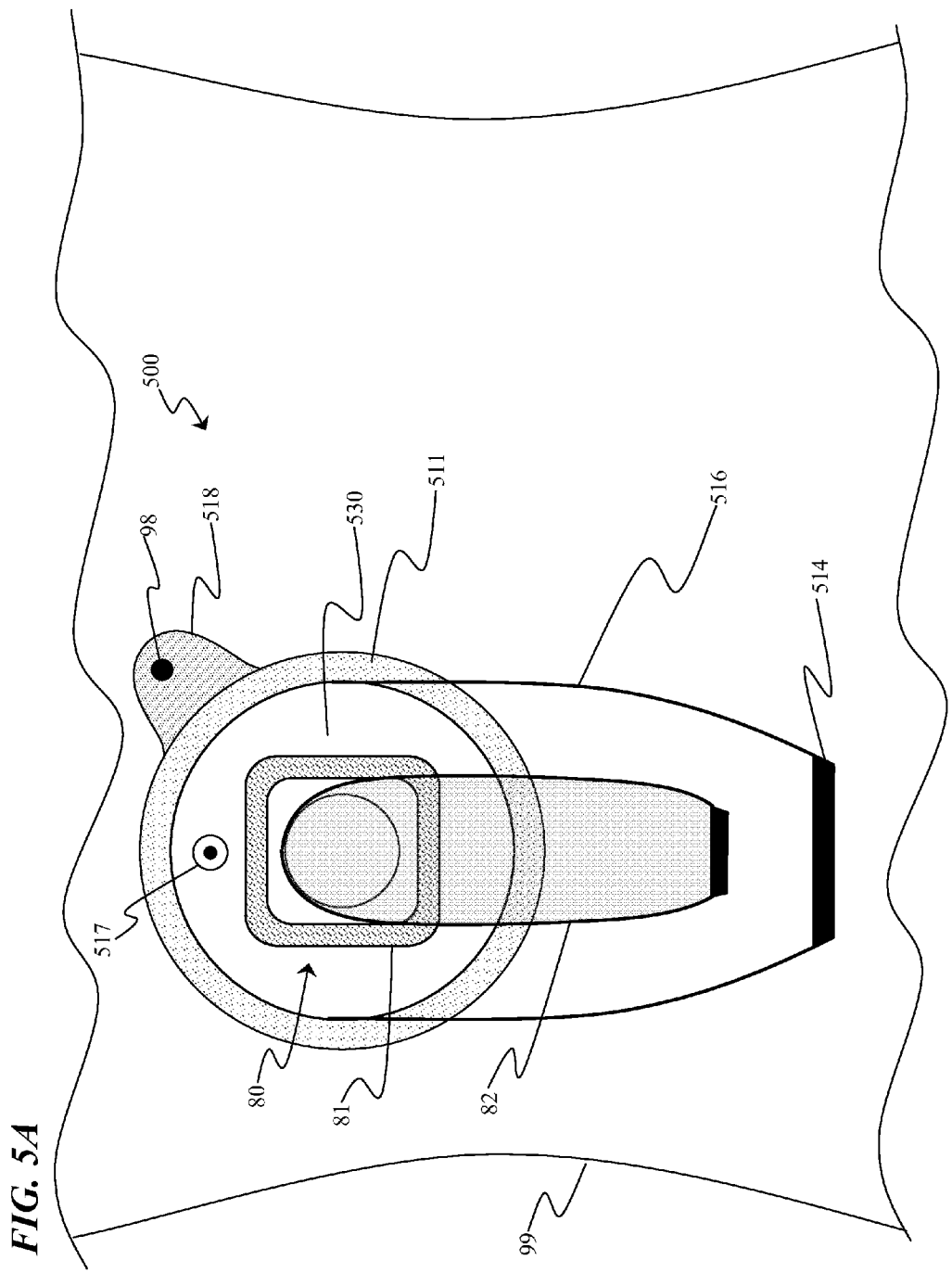
FIG. 5A is a front perspective view of an ostomy-bag-cover system 500, according to other embodiments of the present invention.
Figure 5B:
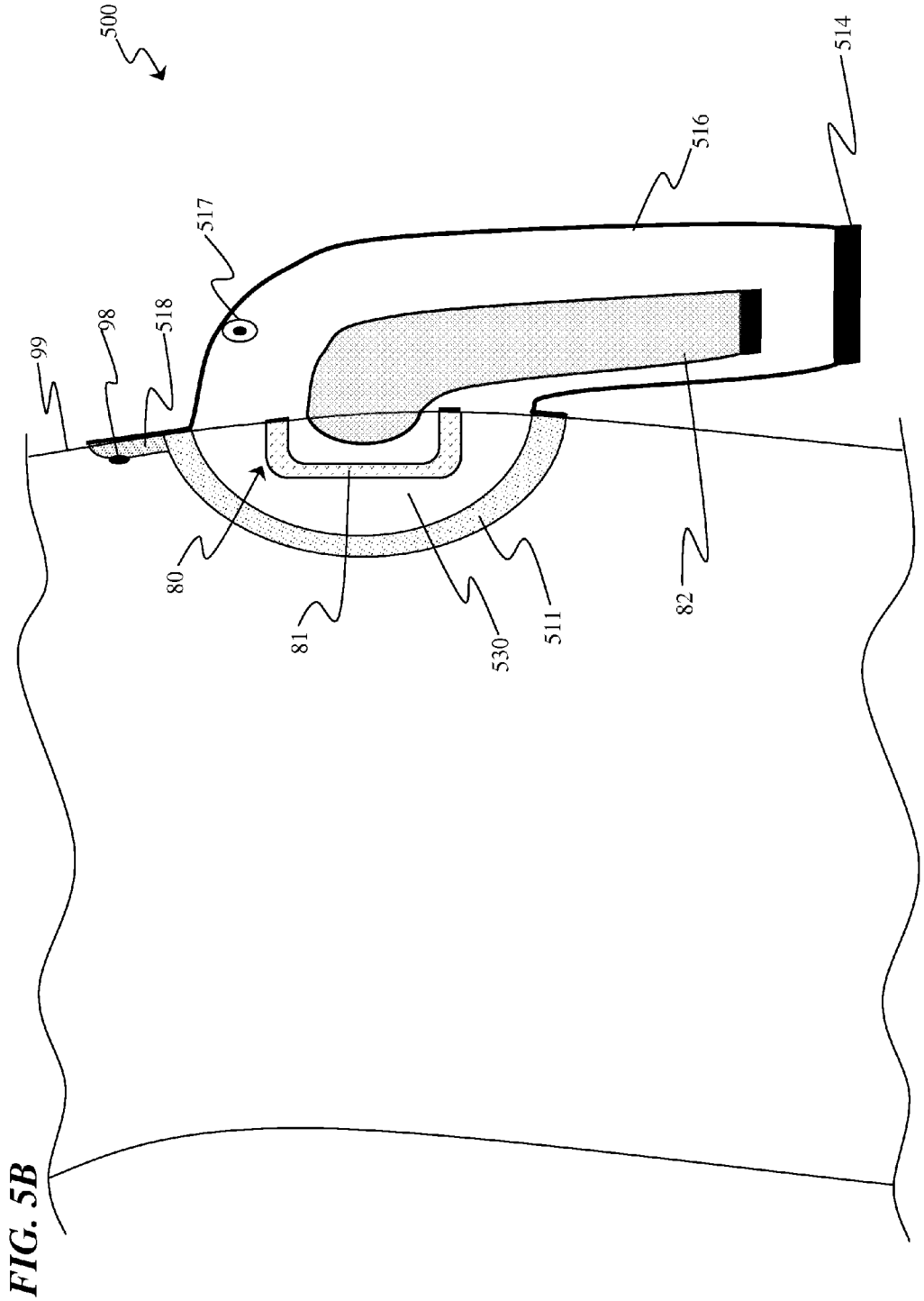
FIG. 5B is a side perspective view of an ostomy-bag-cover system 500, according to other embodiments of the present invention.

FIG. 5A is a front perspective view and FIG. 5B is a side perspective view of an ostomy-bag cover system 500 according to some embodiments of the present invention. The ostomy bag 80, which is not part of the present invention, typically includes a stoma flange 81 with a stoma bag 84 attached to the stoma flange, and wherein a proximal surface of stoma flange 81 is covered with a pressure-sensitive adhesive that adheres to the skin of the abdomen of the patient 99. The ostomy bag 80 is any of several commercially available ostomy bags.

The ostomy-bag cover 500 completely covers the ostomy bag 80, wherein the ostomy-bag cover 500 includes a flange 511 that is attached to a flexible water resistant plastic film cover 516, and wherein the ostomy-bag-cover flange 511 removeably attaches to the skin of the abdomen of the patient 99 with an adhesive on the proximal side of the flange 511 wherein the seal formed by the flange and the skin of the patient is substantially watertight. The ostomy-bag-cover flange 511 is sized in some embodiments to leave free space 530 between the ostomy-bag-cover flange 511 and the stoma flange 81. Further, in other embodiments of the present invention, a tab 518 is attached to the ostomy-bag-cover flange 511 such that the tab 518 is used to cover and seal the perimeter of the area around the navel 98 of the patient 99 when the stoma is located near the navel such that ostomy-bag-cover flange 511 may not adequately seal all of the perimeter of the area around the ostomy bag 80 due to the uneven surface of the skin in the proximity of the navel. If not needed, the ostomy-bag-cover tab 518 can be removed, either by cutting it off, or in some embodiments, torn off along perforations at the connection of the tab and the ostomy-cover flange 511. The ostomy-bag cover 500 keeps water away from the ostomy bag 80 so that in some embodiments, the patient can swim or engage in other water related activities, shower or bathe, without getting his or her ostomy bag wet. In some embodiments, the ostomy-bag cover is single-use, and is removed and disposed of after use.

In some embodiments, the flexible water resistant plastic film cover 516 includes a watertight, one-way, exhaust vent 517 through which any air or other gases inside of the sealed ostomy-bag cover can be removed without the without requiring the patient to remove the ostomy-bag cover, commonly known as "burping" the cover. This makes the ostomy-bag cover less buoyant in water and improves the patient's experience of swimming or participating in other water related activities while wearing an ostomy bag and ostomy-bag cover. In other embodiments, the flexible water resistant plastic film cover 516 includes a resealable opening 514, through which the ostomy bag 80 can be emptied without removing the ostomy-bag cover. When sealed, the resealable opening 514 is watertight so that the ostomy-bag cover provides a watertight cover for the ostomy bag. The resealable opening can be fastened shut using any one of a number of commercially available resealable closures including ziplock plastic bag zipper-style closures, Velcro closures, and clips or other fasteners.

Figure 6A:
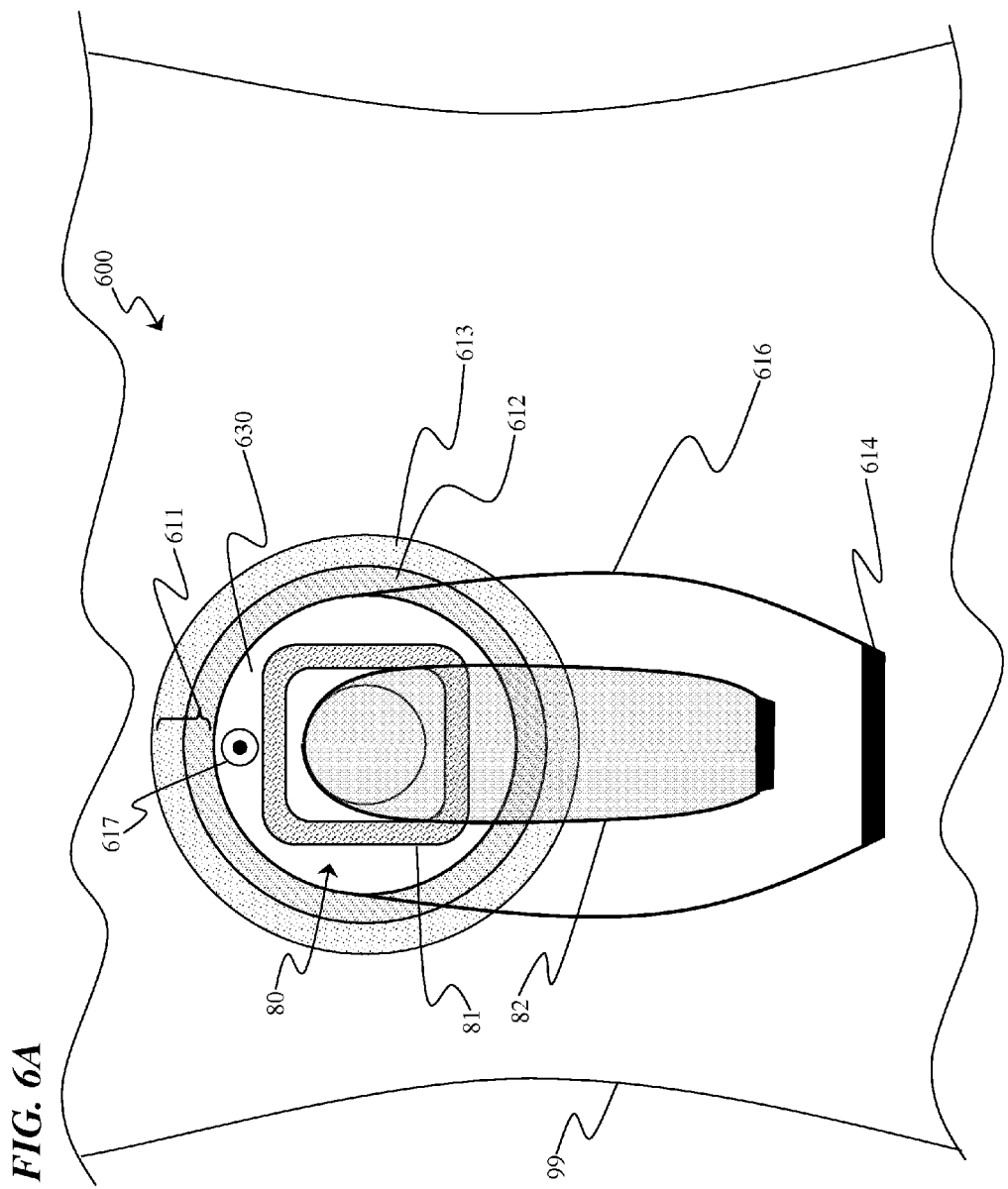
FIG. 6A is a front perspective view of an ostomy-bag-cover system 600, according to other embodiments of the present invention.
Figure 6B:
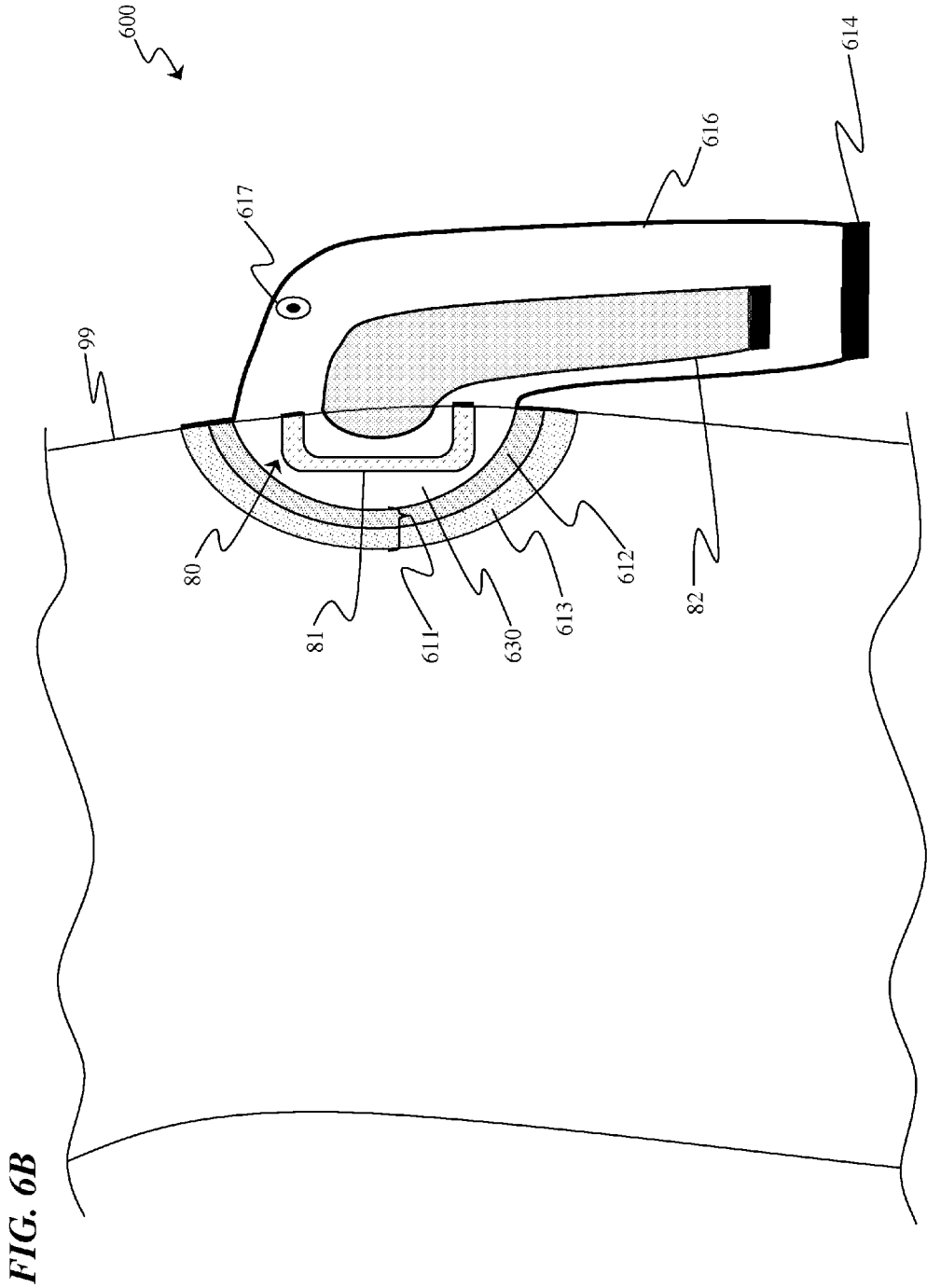
FIG. 6B is a side perspective view of an ostomy-bag-cover system 600, according to other embodiments of the present invention.

FIG. 6A is a front perspective view, and FIG. 6B is a side perspective view, of an ostomy-bag cover system 600, according to other embodiments of the present invention. An ostomy bag 80 is any of several commercially available ostomy bags, wherein the ostomy bag typically comprises a stoma bag 82 which collects patient 99 human waste emitted from the stoma, wherein the stoma bag 82 is attached to the stoma flange 81 and wherein the stoma flange 82 attaches to the abdomen of the patient 99 with an adhesive located on the proximal surface of the stoma flange 81. The ostomy-bag cover 600 includes a flange 611 and a liquid-impermeable flexible cover 616.

In some embodiments, the ostomy-bag-cover flange 611 includes an inner region 612 and an outer region 613, wherein the flange inner region 612 is attached to the liquid-impermeable flexible cover and the proximal (patient-skin) side of the ostomy-bag-cover flange 611 is coated with an adhesive that releasably fastens the ostomy-bag cover to the abdominal skin of the patient 99. The ostomy-bag cover when attached to the patient forms a substantially watertight covering over the ostomy bag 80. In some embodiments, the ostomy-bag-cover flange 611 is of a size that when attached to a patient, some free space (uncovered skin) 630 exists between the ostomy-bag-cover flange 611 and the stoma flange 81.

In some embodiments, the liquid-impermeable flexible cover 616 includes a watertight, one-way, exhaust vent 617 through which any air or other gases inside of the sealed ostomy-bag cover can be removed without the without requiring the patient to remove the ostomy-bag cover, commonly known as "burping" the cover. This makes the ostomy-bag cover less buoyant in water and improves the patient's experience of swimming or participating in other water related activities while wearing an ostomy bag and ostomy-bag cover. In other embodiments, the liquid-impermeable flexible cover 616 includes a resealable opening 614, through which the ostomy bag 80 can be emptied without removing the ostomy-bag cover. When sealed, the resealable opening 614 is watertight so that the ostomy-bag cover provides a watertight cover for the ostomy bag. The resealable opening can be fastened shut using any one of a number of commercially available resealable closures including ziplock plastic bag zipper-style closures, Velcro closures, and clips or other fasteners.

In some embodiments of the present invention, the adhesive coated side of the ostomy-bag-cover flange 611 is protected with at least one thin, easily removable layer of material during shipping to prevent the flange adhesive from adhering to anything prior to being attached to the patient's skin. In some embodiments, the protective material can be paper. In other embodiments, the protective material can be plastic or other thin film. To attach the ostomy-bag cover, the patient first removes the protective layer from the inner region of the ostomy-bag-cover flange 612, and then positions the ostomy-bag cover in the desired location on his or her abdominal skin. The adhesive on the inner region of the flange holds the ostomy-bag cover to the patient's skin and aids in the positioning of the ostomy-bag cover. Once the ostomy-bag cover is positioned as desired, the protective layer from the outer region of the flange 613 is removed and the flange is firmly pressed onto the patient's skin, forming a watertight seal (in addition to any seal that may be provided by the inner region). In the process of attaching the ostomy-bag cover, the ostomy-bag cover may have to be repositioned one or more times, or may flex in handling, resulting in wrinkles in the flange and possibly areas on the flange where the adhesive has become weak. In such cases, the needed watertight seal between the flange and the skin of the patient may be compromised. The additional adhesive on the outer portion of the flange, which is not exposed until the ostomy-bag cover is positioned on the patient's skin, ensures a good seal between the flange and the skin once the inner region is properly positioned and the release material has been removed from the outer region.

Figure 7:
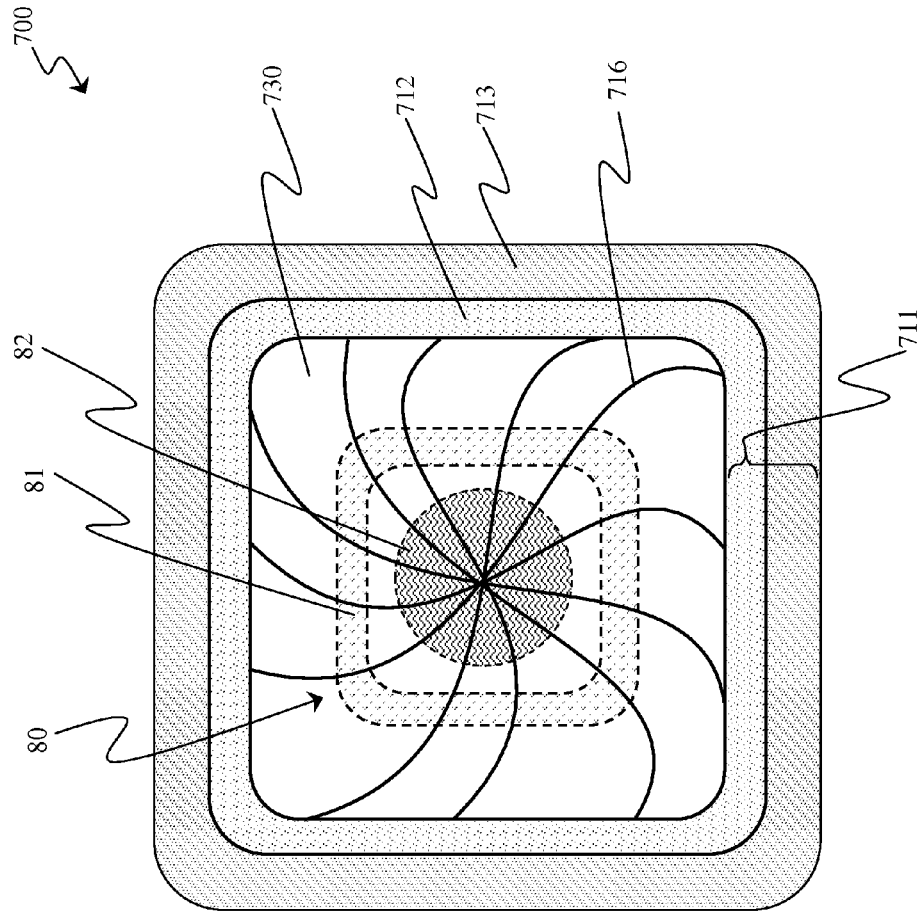
FIG. 7 is a front perspective view of an ostomy-bag-cover system 700, according to other embodiments of the present invention.

The ostomy-bag-cover flange can be produced in a variety of shapes, to better suit the needs of particular patients. FIG. 7 is a front perspective view of an ostomy-bag cover system 700, according to other embodiments of the present invention. An ostomy bag 80 is any of several commercially available ostomy bags, wherein the ostomy bag typically includes a stoma bag 82 which collects patient 99 human waste emitted from the stoma, wherein the stoma bag 82 is attached to the stoma flange 81 and wherein the stoma flange 81 attaches to the abdomen of the patient 99 with an adhesive located on the proximal surface of the stoma flange 81. The ostomy-bag cover 700 completely covers the ostomy bag 80, wherein the ostomy-bag cover 700 includes an ostomy-bag-cover flange 711 with an inner region 712 and an outer region 713. In some embodiments, the ostomy-bag-cover flange 711 is shaped as a square with rounded corners. The inner region of the flange 712 is attached to a flexible plastic film cover 716, and the ostomy-bag-cover flange 711 removeably attaches to the abdomen of the patient 99 with an adhesive on the proximal side of the flange 711, wherein the seal formed by the flange and the skin of the patient is substantially watertight. The ostomy-bag-cover flange 711 is sized in some embodiments to leave free space 730 between the ostomy-bag-cover flange 711 and the stoma flange 81. The ostomy-bag cover 700 keeps water away from the ostomy bag 80 so that in some embodiments, the patient can shower or bathe without getting his or her ostomy bag wet.

Figure 8:
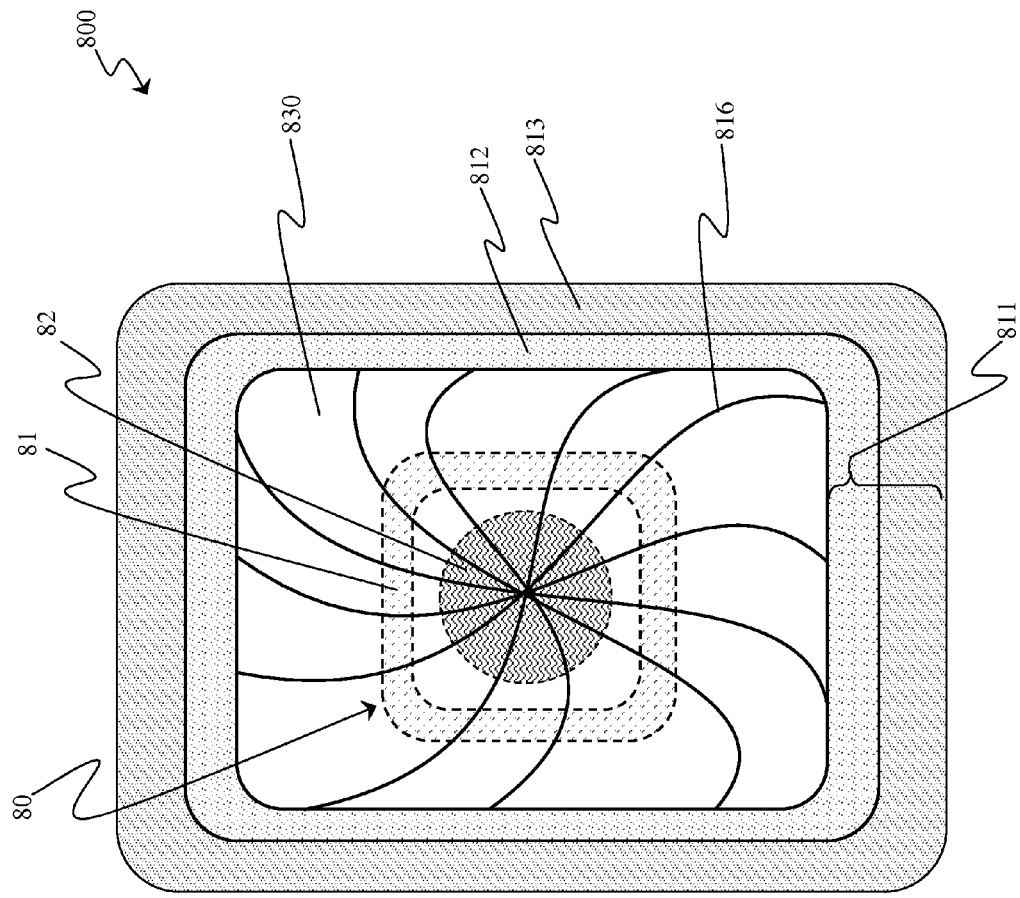
FIG. 8 is a front perspective view of an ostomy-bag-cover system 800, according to other embodiments of the present invention.

FIG. 8 is a front perspective view of an ostomy-bag cover system 800, according to other embodiments of the present invention. An ostomy bag 80 is any of several commercially available ostomy bags, wherein the ostomy bag typically includes a stoma bag 82 which collects patient 99 human waste emitted from the stoma, wherein the stoma bag 82 is attached to the stoma flange 81 and wherein the stoma flange 81 attaches to the abdomen of the patient 99 with an adhesive located on the proximal surface of the stoma flange 81. The ostomy-bag cover 800 completely covers the ostomy bag 80, wherein the ostomy-bag cover 800 includes an ostomy-bag-cover flange 811 with an inner region 812 and an outer region 813. In some embodiments, the ostomy-bag-cover flange 811 is shaped as a rectangle with rounded corners. The inner region of the flange 812 is attached to a flexible plastic film cover 816, and the ostomy-bag-cover flange 811 removeably attaches to the abdomen of the patient 99 with an adhesive on the proximal side of the flange 811, wherein the seal formed by the flange and the skin of the patient is substantially watertight. The ostomy-bag-cover flange 811 is sized in some embodiments to leave free space 830 between the ostomy-bag-cover flange 811 and the stoma flange 81. The ostomy-bag cover 800 keeps water away from the ostomy bag 80 so that in some embodiments, the patient can shower or bathe without getting his or her ostomy bag wet.

Figure 9:
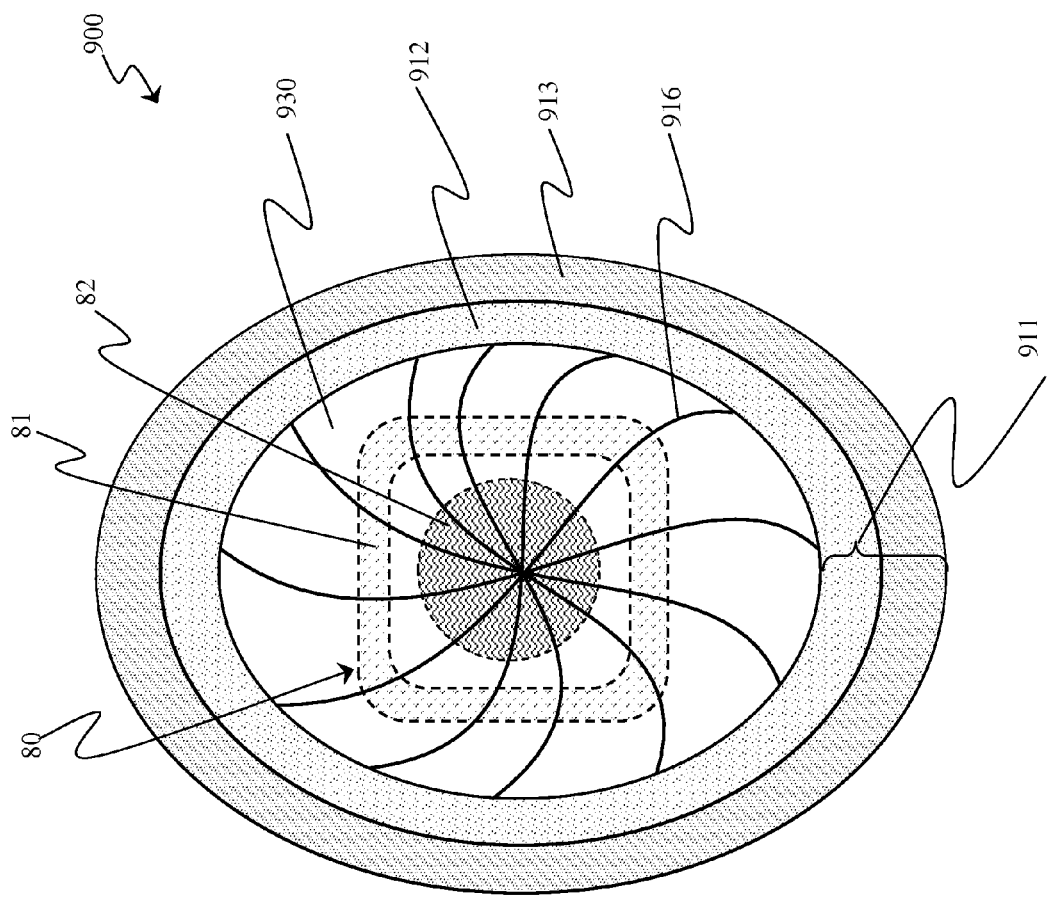
FIG. 9 is a front perspective view of an ostomy-bag-cover system 900, according to other embodiments of the present invention.

FIG. 9 is a front perspective view of an ostomy-bag cover system 900, according to other embodiments of the present invention. An ostomy bag 80 is any of several commercially available ostomy bags, wherein the ostomy bag typically includes a stoma bag 82 which collects patient 99 human waste emitted from the stoma, wherein the stoma bag 82 is attached to the stoma flange 81 and wherein the stoma flange 81 attaches to the abdomen of the patient 99 with an adhesive located on the proximal surface of the stoma flange 81. The ostomy-bag cover 900 completely covers the ostomy bag 80, wherein the ostomy-bag cover 900 includes an ostomy-bag-cover flange 911 with an inner region 912 and an outer region 913. In some embodiments, the ostomy-bag-cover flange 911 is shaped as an oval. The inner region of the flange 912 is attached to a flexible plastic film bag cover 916, and the ostomy-bag-cover flange 911 removeably attaches to the abdomen of the patient 99 with an adhesive on the proximal side of the flange 911, wherein the seal formed by the flange and the skin of the patient is substantially watertight. The ostomy-bag-cover flange 911 is sized in some embodiments to leave free space 930 between the ostomy-bag-cover flange 911 and the stoma flange 81. The ostomy-bag cover 900 keeps water away from the ostomy bag 80 so that in some embodiments, the patient can shower or bathe without getting his or her ostomy bag wet.

As used herein, annulus shaped is shaped as the area between two circles in a plane.

As used herein, tubular shaped is shaped as a wall that is connected to itself, and can include the wall conforming to and surrounding a pyramid or conical frustum, the walls surrounding a cylinder, or the like.

In some embodiments, the present invention is an apparatus for covering an ostomy bag and its ostomy-bag-flange, the apparatus includes a bag formed from a polymer film that covers ostomy bag and its ostomy-bag-flange, the bag having a proximal end and a distal end. The apparatus further includes a cover flange having a distal side and a proximal side, wherein the distal side of the cover flange is connected to the top end of the bag forming a substantially waterproof seal between the cover flange and the top of the bag, wherein the proximal side of the cover flange is coated with an adhesive that releasably attaches the proximal side of the cover flange to a patient wearing an ostomy-bag-and-flange and forms a substantially waterproof seal between the flange and the skin of the patient, and wherein the flange contains an opening approximately centered in the flange that is large enough for the flange to surround the ostomy-bag-flange without contacting the ostomy-bag-flange. The cover bag and cover flange form a substantially waterproof cover over the ostomy-bag-and-flange.

As used wherein, a "type of polymer film" includes the chemical composition as well as the thickness, number of plies or sub-layers, texture, durometer, stiffness, opacity, adhesion quality and other characteristics of the film. The type of polymer film may also include any coatings such as metallic films, adhesives, release agents, anti-microbial agents, and the like. The type of polymer film may also include polymer foam material. Accordingly different types of polymer films may include different chemical compositions, but also include films having identical compositions but having different thicknesses, textures, durometers, stiffnesses, opacities, adhesion qualities, foam/solid (number or size of air pockets in the material) or other characteristics.

In some embodiments, the cover bag or body of the present invention is coated with an anti-microbial agent or metal film. In some embodiments, the body is texturized or corrugated to provide enhanced expandability and stretchiness. In some embodiments, the flange portion is formed as a thicker film and/or a film having more plies than the film of the body for improved durability and tear resistance. In some embodiments, the body of the cover is coated with a release agent in order to prevent it sticking to the adhesive of the flange, as well as allowing multiple covers to be stacked without sticking to one another, as well as facilitating unfolding of a single bag that has been folded for enhanced compact packaging. In some embodiments, the polymer film of the flange is made stiffer than the film of the body to enhance handle-ability of the flange while maintaining flexibility and expandability of the cover's body. In some embodiments, the flange and/or body is made opaque or translucent for aesthetic reasons. In other embodiments, the flange is made transparent in order that the patient may visually inspect the seal to her or his skin. In some embodiments, the flange of the ostomy-bag cover is coated with one or more types of pressure-sensitive hypoallergenic adhesive, which in turn is covered a removable release film, also known as a backing or protective cover.

In some embodiments, a plurality of ostomy-bag covers are provided wherein each ostomy-bag cover is enclosed in its own wrapper made of, e.g., paper, cardboard, plastic, foil and/or the like. In some embodiments, the wrapper is imprinted with a decorative design to promote the brand name and/or to disguise the contents.

In some embodiments, the present invention includes a resealable opening at the bottom of the bag wherein the opening the patient to remove excess air in the bag covering the ostomy-bag-and-flange, and wherein the opening can be sealed to prevent water from entering the bag. In other embodiments, the resalable opening at the bottom of the bag can be used to empty the ostomy bag without removing the bag and its attached flange.

In some embodiments, the cover flange is shaped substantially like an annulus. In other embodiments, the cover flange can be shaped as a square or rectangle with rounded corners. In other embodiments, the cover flange can be shaped as an oval.

In other embodiments, the bag and attached cover flange form a single-use, substantially waterproof cover over the ostomy-bag-and-flange for use in a shower wherein the patient can shower without the need to dry the ostomy bag and its ostomy-bag flange, or to remove the ostomy bag during the shower.

In other embodiments, the present invention provides a bag formed from a flexible waterproof material, the bag having a top end and a bottom end, and fashioned to cover an ostomy-bag-and-flange. The present invention further provides a flange having a distal side and a proximal side, wherein the distal side of the flange is connected to the top end of the bag forming a substantially waterproof seal between the flange and the top of the bag, wherein the proximal side is coated with an adhesive that releasably attaches the proximal side of the flange to a patient wearing an ostomy-bag-and-flange and forms a substantially waterproof seal between the flange and the skin of a patient, and wherein the flange contains an opening approximately centered in the flange that is large enough for the flange to surround the ostomy-bag-flange without contacting the ostomy-bag-flange. A resealable opening is provided at the bottom of the bag wherein the opening allows a patient to remove excess air in the bag covering the ostomy-bag-and-flange, and wherein the opening can be sealed to prevent water from entering the bag. The bag and flange form a substantially waterproof cover over the ostomy-bag-and-flange.

In some embodiments, the present invention is an apparatus for protectively covering an ostomy bag of a patient, wherein the ostomy bag has an ostomy-bag flange, and the ostomy-bag flange adheres to the patient's skin surrounding a stoma. The present invention includes an ostomy-bag cover having a cover-side portion formed from a polymer film, the cover-side portion having a tubular body, a proximal end opening and a distal end opening, wherein the ostomy-bag cover covers the ostomy bag and its ostomy-bag flange in order to inhibit water from reaching the ostomy bag and its ostomy-bag flange. In some embodiments, the present invention further includes a cover-flange portion connected to the cover-side portion and surrounding the proximal end opening, the cover-flange portion having a patient-skin-contact side and a distal side, wherein the patient-skin-contact side has a pressure-sensitive adhesive that releasably attaches the proximal side of the flange to the patient's skin surrounding the ostomy-bag flange and forms a water-resistant seal to the patient's skin, and wherein the cover-flange portion contains an opening that is large enough for the cover-flange portion to surround the ostomy-bag-flange without contacting the ostomy-bag-flange. The present invention further includes a resealable vent at the distal end of the cover-side portion, wherein the vent facilitates removal of excess air within the ostomy-bag cover surrounding the ostomy bag and its ostomy-bag flange, wherein the vent is sealable to prevent water from entering the ostomy-bag cover, and whereby the ostomy-bag cover forms a water-resistant cover over the ostomy bag and its ostomy-bag flange.

In some embodiments, the present invention provides an apparatus kit for covering an ostomy bag of a patient, the ostomy bag having an ostomy-bag flange, wherein the ostomy-bag flange adheres to the patient's skin surrounding a stoma. The apparatus kit includes an ostomy-bag-cover body, wherein the ostomy-bag-cover body includes: a protective covering formed from a liquid-impermeable membrane, wherein the protective covering is substantially flat before use, and wherein the protective covering unfolds to fit over the ostomy bag and its ostomy-bag flange and a cover-flange portion connected to the protective covering, the cover-flange portion having a patient-skin-contact side and a distal side. The kit further includes an adhesive-attachment band, the adhesive-attachment band having a first surface with a pressure-sensitive adhesive, and a second surface with a pressure-sensitive adhesive, wherein the adhesive-attachment band is shaped approximately the same as the cover-flange, wherein the pressure-sensitive adhesive of the first side of the adhesive-attachment band is covered by a first removable piece of release film, and the pressure-sensitive adhesive of the second side of the adhesive-attachment band is covered by a second removable piece of release film, wherein the adhesive-attachment band releasably attaches to an area of the patient's skin surrounding the ostomy-bag flange and to the patient-skin-contact side of the cover-flange in order to form a watertight seal to an area of the patient's skin that surrounds the ostomy-bag-flange.

In some embodiments, the adhesive-attachment band includes a polymer film having the pressure-sensitive adhesive on both of two major faces of the film.

In some embodiments, the adhesive-attachment band is constructed, at least in part, of paper.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus for covering an ostomy bag of a patient, the ostomy bag having an ostomy-bag flange, wherein the ostomy-bag flange adheres to the patient's skin surrounding a stoma, the apparatus comprising:
    an ostomy-bag cover, wherein the ostomy-bag cover covers the ostomy bag and its ostomy-bag flange in order to prevent water from reaching the ostomy bag and its ostomy-bag flange, the ostomy-bag cover having:
    a body formed from a liquid-impermeable membrane, the body having a proximal end opening and a distal end opening;
    a cover-flange portion connected to the proximal end opening of the body, the cover-flange portion having a patient-skin-contact side and a distal side, wherein the patient-skin-contact side has a pressure-sensitive adhesive that releasably attaches the patient-skin-contact side of the flange to the patient's skin surrounding the ostomy-bag flange and forms a watertight seal to an area of the patient's skin that surrounds the ostomy-bag-flange; and
    a sealable exhaust vent, wherein the vent is operable to remove excess air within the ostomy-bag cover while the cover-flange portion is sealed to the patient's skin, wherein the vent prevents water from entering the ostomy-bag cover, in order that the ostomy-bag cover forms a watertight cover over the ostomy bag and its ostomy-bag flange,
wherein the cover-flange portion includes at least a first flap extension of the cover-flange portion to cover the umbilicus of the patient.

2. The apparatus of claim 1, wherein the cover-flange portion is annulus shaped.

3. The apparatus of claim 1, wherein the ostomy-bag cover further includes resealable opening at the distal end of the body of the ostomy-bag cover, wherein the resealable opening is operable to empty the ostomy bag without removing the ostomy bag cover.

4. The apparatus of claim 1, wherein the sealable exhaust vent forms a resealable opening at the distal end of the body of the ostomy-bag cover, wherein the resealable opening is operable to empty the ostomy bag without removing the ostomy bag cover.

5. The apparatus of claim 1, wherein the ostomy-bag cover forms a single-use, disposable, waterproof cover over the ostomy bag and its ostomy-bag flange.

6. The apparatus of claim 1, wherein the cover-flange portion is constructed of a first type of polymer film, wherein the body is constructed of a second type of polymer film different than the first type of polymer film, and wherein the polymer film of the flange is fused to the polymer film of the body.

7. The apparatus of claim 1, wherein the liquid-impermeable membrane forming the body and the adhesive on the cover-flange portion are configured to allow the patient to swim while wearing the ostomy-bag cover.

8. The apparatus of claim 1, wherein the ostomy-bag cover further includes a removable peel-away covering over the adhesive on the flange, and wherein the ostomy-bag cover is enclosed within a removable disposable wrapper.

9. The apparatus of claim 1, wherein the cover flange has an inner diameter of between about ten cm and about twelve cm, and has a flange width of about 1 cm that is covered with the pressure-sensitive adhesive.

10. The apparatus of claim 1, wherein the flange is rectangular with rounded corners.

11. An apparatus for covering an ostomy bag of a patient, the ostomy bag having an ostomy-bag flange, wherein the ostomy-bag flange adheres to the patient's skin surrounding a stoma, the apparatus comprising:
    an ostomy-bag cover, wherein the ostomy-bag cover covers the ostomy bag and its ostomy-bag flange in order to prevent water from reaching the ostomy bag and its ostomy-bag flange, the ostomy-bag cover having:
    a body formed from a liquid-impermeable membrane, the body having a proximal end opening and a distal end opening;
    a cover-flange portion connected to the proximal end opening of the body, the cover-flange portion having a patient-skin-contact side and a distal side, wherein the patient-skin-contact side has a pressure-sensitive adhesive that releasably attaches the patient-skin-contact side of the flange to the patient's skin surrounding the ostomy-bag flange and forms a watertight seal to an area of the patient's skin that surrounds the ostomy-bag-flange; and
    a sealable exhaust vent, wherein the vent is operable to remove excess air within the ostomy-bag cover while the cover-flange portion is sealed to the patient's skin, wherein the vent prevents water from entering the ostomy-bag cover, in order that the ostomy-bag cover forms a watertight cover over the ostomy bag and its ostomy-bag flange,
wherein the pressure-sensitive adhesive of the cover flange has a first annular region covered by at least one first removable piece of release film, and a second annular region that is concentric to the first annular region and covered by at least one second removable piece of release film.

12. A method for covering for an ostomy bag of a patient with an ostomy-bag cover, the ostomy bag having an ostomy-bag flange, wherein the ostomy-bag flange adheres to the patient's skin surrounding a stoma, wherein the ostomy-bag cover covers the ostomy bag and its ostomy-bag flange in order to restrict water from reaching the ostomy bag and its ostomy-bag flange, the method comprising:
    providing a tubular body of the ostomy-bag cover from a liquid-impermeable membrane, the tubular body having a proximal end opening and a distal end opening, wherein the ostomy-bag cover covers the ostomy bag and its ostomy-bag flange in order to prevent water from reaching the ostomy bag and its ostomy-bag flange;
    providing a cover-flange portion connected to the proximal end opening of the tubular body, the cover-flange portion having a proximal side and a distal side, wherein the proximal side has a pressure-sensitive adhesive;

providing a resealable opening at the distal end of the tubular body;

adhering at least a first annular region of the proximal side of the cover-flange portion of the ostomy-bag cover to the patient with the pressure-sensitive adhesive forming a watertight seal to the patient's skin, wherein the ostomy-bag cover forms a waterproof cover over the ostomy bag and its ostomy-bag flange;

sealing the resealable opening to prevent water from entering the ostomy-bag cover;

providing at least one first removable peel-away covering over the adhesive on the first annular region of the cover flange;

providing at least one second removable peel-away covering over the adhesive on a second annular region of the cover flange that is concentric to, and outside of, the first annular region of the cover flange; and adhering the second annular region of the proximal side of the cover-flange portion of the ostomy-bag cover to the patient after adhering the first annular region to the patient.

13. The method of claim 12, further comprising: emptying of the ostomy bag through the resealable opening at the distal end of the tubular body of the ostomy-bag cover, without removing the ostomy bag cover from the patient's skin.

14. The method of claim 12, wherein the liquid-impermeable membrane includes a polymer film.

15. The method of claim 12, further comprising:

providing a water-proof one-way vent in the tubular body; and expelling excess air within the ostomy-bag cover through the one-way vent while the ostomy-bag cover is adhered to the patient.

16. An apparatus for covering an ostomy bag of a patient, the ostomy bag having an ostomy-bag flange, wherein the ostomy-bag flange adheres to the patient's skin surrounding a stoma, the apparatus comprising:

protective film means for covering the ostomy bag and its ostomy-bag flange in order to prevent water from reaching the ostomy bag and its ostomy-bag flange;

pressure-sensitive adhesive flange means for attaching the protective film means to a patient, wherein the means for attaching is connected to the means for covering, wherein the means for attaching has an opening that is large enough for the means for attaching to adhere to the patient's skin surrounding the ostomy-bag-flange without contacting the ostomy-bag-flange, and wherein the means for attaching includes a first means for exposing the adhesive on a first region of the means for attaching and at least a second means for exposing the adhesive on a second region of the means for attaching, wherein the means for covering includes a means for exhausting air from the means for covering other than the opening; and folding means for flattening the means for covering and the means for attaching, such that the means for covering and means for attaching are flat before use, and such that the means for covering readily unfolds to fit over the ostomy bag and its ostomy-bag flange.

17. The apparatus of claim 16, further comprising means for extending the water-resistant seal of the flange to further cover the patient's umbilicus.

18. The apparatus of claim 16, further comprising removable means for protecting the means for attaching.

19. The apparatus of claim 18, further comprising:

first removable means for protecting a first annular region of the means for attaching to allow the ostomy-bag cover to be positioned and adhered to the patient's skin; and second removable means for protecting a second annular region surrounding the first annular region to allow the ostomy-bag cover to be better sealed to the patient's skin.

20. An apparatus for covering an ostomy bag of a patient, the ostomy bag having an ostomy-bag flange, wherein the ostomy-bag flange adheres to the patient's skin surrounding a stoma, the apparatus comprising:

a protective covering formed from a liquid-impermeable membrane, wherein the protective covering is flat before use, and wherein the protective covering unfolds to fit over the ostomy bag and its ostomy-bag flange; and a cover-flange portion connected to the protective covering, the cover-flange portion having a patient-skin-contact side and a distal side, wherein the patient-skin-contact side includes a pressure-sensitive adhesive that releasably attaches the patient-skin-contact side of the cover-flange to an area of the patient's skin surrounding the ostomy-bag flange and forms a watertight seal to an area of the patient's skin that surrounds the ostomy-bag-flange; and wherein the pressure-sensitive adhesive of the cover flange has a first annular region covered by a first removable piece of release film, and a second annular region that is concentric to the first annular region and covered by a second removable piece of release film.

21. The apparatus of claim 20, wherein the cover-flange portion includes at least a first flap extension to cover at least the umbilicus of the patient.

22. The apparatus of claim 20, wherein the ostomy-bag cover forms a single-use, disposable, waterproof cover over the ostomy bag and its ostomy-bag flange.

23. The apparatus of claim 20, wherein the cover-flange portion is constructed of a first type of polymer film, wherein the body is constructed of a second type of polymer film different than the first type of polymer film, and wherein the polymer film of the flange is fused to the polymer film of the body.

24. An apparatus kit for covering an ostomy bag of a patient, the ostomy bag having an ostomy-bag flange, wherein the ostomy-bag flange adheres to the patient's skin surrounding a stoma, the apparatus kit comprising:

an ostomy-bag-cover body, wherein the ostomy-bag-cover body includes:

a protective covering formed from a liquid-impermeable membrane, wherein the protective covering is flat before use, and wherein the protective covering unfolds to fit over the ostomy bag and its ostomy-bag flange, and a cover-flange portion connected to the protective covering, the cover-flange portion having a patient-skin-contact side and a distal side; and an adhesive-attachment band, the adhesive-attachment band having a first surface with a pressure-sensitive adhesive, and a second surface with a pressure-sensitive adhesive, wherein the adhesive-attachment band is shaped approximately the same as the cover-flange, wherein the pressure-sensitive adhesive of the first side of the adhesive-attachment band is covered by a first removable piece of release film, and the pressure-sensitive adhesive of the second side of the adhesive-attachment band is covered by a second removable piece of release film, wherein the adhesive-attachment band releasably attaches to an area of the patient's skin surrounding the ostomy-bag flange and to the patient-skin-contact side of the cover-flange in order to form a watertight seal to an area of the patient's skin that surrounds the ostomy-bag-flange.

25. The apparatus of claim 24, wherein the adhesive-attachment band includes a polymer film having the pressure-sensitive adhesive on both of two major faces of the film.

26. The apparatus of claim 24, where in the adhesive-attachment band is constructed, at least in part, of paper.

* * * * *